United States Patent
Watanabe et al.

(10) Patent No.: US 6,573,279 B1
(45) Date of Patent: Jun. 3, 2003

(54) ISOQUINOLINE DERIVATIVES OR SALTS THEREOF

(76) Inventors: Toshihiro Watanabe, c/o Yamanouchi Pharmaceutical Co., Ltd., 21, Miyukigaoka, Tsukuba-shi, Ibaraki 305-8585 (JP); Akio Kakefuda, c/o Yamanouchi Pharmaceutical Co., Ltd., 21, Miyukigaoka, Tsukuba-shi, Ibaraki 305-8585 (JP); Toshio Okazaki, c/o Yamanouchi Pharmaceutical Co., Ltd., 21, Miyukigaoka, Tsukuba-shi, Ibaraki 305-8585 (JP); Noriyuki Masuda, c/o Yamanouchi Pharmaceutical Co., Ltd., 21, Miyukigaoka, Tsukuba-shi, Ibaraki 305-8585 (JP); Koichi Wada, c/o Yamanouchi Pharmaceutical Co., Ltd., 21, Miyukigaoka, Tsukuba-shi, Ibaraki 305-8585 (JP)

( * ) Notice: Subject to any disclaimer, the term of this patent is extended or adjusted under 35 U.S.C. 154(b) by 41 days.

(21) Appl. No.: 09/980,402
(22) PCT Filed: Jun. 1, 2000
(86) PCT No.: PCT/JP00/03564
  § 371 (c)(1),
  (2), (4) Date: Dec. 3, 2001
(87) PCT Pub. No.: WO00/75133
  PCT Pub. Date: Dec. 14, 2000

(30) Foreign Application Priority Data

Jun. 3, 1999 (JP) .......................................... 11-156217

(51) Int. Cl.⁷ ................................................ A61K 31/47
(52) U.S. Cl. ........................ 514/307; 514/308; 514/309
(58) Field of Search ................................ 514/307, 308, 514/309

(56) References Cited

FOREIGN PATENT DOCUMENTS

| JP | 02138172 | 5/1990 |
| WO | WO98/13364 | 4/1998 |

*Primary Examiner*—Zohreh Fay
*Assistant Examiner*—Brian-Yong S. Kwon

(57) ABSTRACT

The compound of the present invention relates to a drug, particularly to a novel isoquinoline derivative or its salt having an $I_f$ current inhibitory effect without serious side effects such as convulsion and also to a drug, particularly a cardiac rate lowering agent, containing the compound as the active ingredient. Namely, the compound has a current $I_f$ inhibitory effect and is particularly useful as a cardiac rate lowering agent for preventing ischemic heart diseases such as angina and cardiac infarction and circulatory diseases such as congestive cardiac insufficiency and arrhythmia (supraventricular arrhythmia). The present invention relates to dialkoxy-1,2,3,4-tetrahydroquinoline-2-carbonylpiperidino-3,4-dialkoxypropaneanilide derivatives, etc.

6 Claims, No Drawings

ISOQUINOLINE DERIVATIVES OR SALTS THEREOF

This Application is a 371 of PCT/JP00/03564 Jun. 1, 2000.

TECHNICAL FIELD

The present invention relates to drugs, particularly to novel isoquinoline derivatives or salts having a $I_f$ current inhibitory effect without serious side effects such as convulsion and also to drugs, particularly cardiac rate lowering agents containing these compounds as the active ingredient.

BACKGROUND OF THE INVENTION

With regard to drugs having a cardiac rate lowering effect, there have been known neurotransmitter receptors and drugs acting on ion channels, and representative examples of the former are adenosine receptor agonists, $M_2$ muscarinic receptor agonists and β-adrenergic receptor antagonists, while those of the latter are calcium channel blockers. Such drugs which lower the cardiac rate have been confirmed to be useful as preventive and therapeutic agents for various clinical symptoms caused by imbalance between supply and demand of oxygen in cardiac muscles, for example, ischemic heart diseases such as angina and cardiac infarction and circulatory diseases such as arrhythmia and cardiac insufficiency. However, these drugs have not only a cardiac rate lowering effect but also an excessive suppressing effect to atrioventricular conduction and systolic function or a hypotensive effect. In some cases, they may express an action which results in a complete cardiac arrest and, therefore, their use especially to patients whose cardiac function lowers has been worried about.

On the other hand, it has been known that electrical excitation spontaneously takes place in sinoatrial node having a physiological cardiac pacemaker action, atrioventricular node constituting conduction system and cells such as His bundle and Purkinje fiber. In the cells having a cardiac pacemaker action, there has been confirmed the presence of an ionic current having no selectivity in permeation to cations such as sodium ion and potassium ion, being activated by hyperpolarization of membrane potential and being activated by stimulation with a β receptor, which is named a $I_f$ current (Difrancesco, D., et al., *J. Physiol.*, 377:61–88, 1986; Irisawa, H., et al., *Physiol. Rev.*, 73:197–227, 1993; and Difracesco, D., *Annu. Rev. Physiol.*, 55:455–472, 1993). It is believed that, in heart, the $I_f$ current is a current which contributes in the formation of diastolic depolarization of the cells having a pacemaker effect and carries out cardiac rate adjustment.

Accordingly, there has been expected an effect of lowering the cardiac rate by inhibiting the $I_f$ current regulating the inclination of the diastolic depolarization. In fact, pharmaceuticals of a new type which express the cardiac rate lowering effect by inhibiting the $I_f$ current have been reported recently. Such $I_f$ current inhibitors are able to selectively lower the cardiac rate without excessive suppression of atrioventricular conduction and systolic function and also able to reduce the oxygen consumption of cardiac muscle. Accordingly, the current $I_f$ inhibitors are discriminated from the activity of the conventional various receptor agonists and calcium channel blockers due to the absence of an excessive suppressing effect to atrioventricular conduction and systolic function or of a cardiac arrest effect. Therefore, the $I_f$ current inhibitors are expected to be able to be preventive and therapeutic agents for ischemic diseases (such as angina and cardiac infarction) and circulatory diseases (such as arrhythmia and cardiac insufficiency) with little side effects. They are also useful to suppress an excessively increased cardiac rate so as to control the cardiac rate to a predetermined state in operations under anesthesia, etc.

It has been further reported that an ionic current having a similar property to the $I_f$ current (having no selectivity in permeation to cations, being activated by hyperpolarization and being activated by stimulation with a β receptor) is present not only in the cells having a pacemaker effect but also in inherent cardiac muscle cells usually having no pacemaker effect such as atrial muscle and ventricular muscle cells (Hangang Yu, *Circ. Res.*, 72:232–236, 1993). In some types of symptoms of cardiac insufficiency, hypertension or the like, electrical excitation is spontaneously resulted even in the intrinsic cardiac muscle cells and, when effect potential is recorded from those cells, there is observed diastolic depolarization where membrane potential is gradually depolarized during the electrical diastole after the effect potential is repolarized. In such symptom, an increase in the $I_f$ current is confirmed, and it is presumed that the $I_f$ current contributes in the formation of this diastolic depolarization causing acceleration of ectopic automatism or triggered activity (Elizabetta, C., et al., *Circulation*, 94:1674–1681, 1996; and Elizabetta, C., et al., *Circulation*, 95:568–571, 1997). Accordingly, it has been believed that the $I_f$ current inhibitors are useful for the suppression of the acceleration of ectopic automatism or triggered activity in those symptoms.

It has been known that the effect of zatebradine which is known as a compound having a cardiac rate lowering effect is based on the $I_f$ current inhibitory effect. However, it has been reported that zatebradine expresses a cardiac rate lowering effect and a visual disorder (William H. Frishman, *J. Am. Coll. Cardiol.*, 26:305–312, 1995; and Stephen P. Glasser, et al., *The American Journal of Cardiology*, 79:1401–1405, 1997). It has been known that another current ($I_h$ current) having a similar property to the $I_f$ current is present in visual cells (Shaul Hestrin, *J. Physiol.*, 390:319–333, 1987). But, since zatebradine inhibits the $I_h$ current together with the $I_f$ current, such visual disorder is presumed to be expressed thereby. In the study of the $I_f$ current inhibitors, separation from the $I_h$ current inhibitory effect is one of the propositions.

With regard to the compound having an anti-tachycardiac effect or a vasodilating effect, β-amino acid amide derivatives represented by the following general formula have been reported (Japanese Patent Laid-Open No. 138172/1990). However, there is no description for the $I_f$ current inhibitory effect.

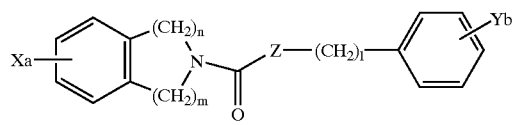

(As to the symbols in the formula, refer to the above-mentioned patent.)

In addition, the present inventors have reported that 2-(3-piperidyl)-1,2,3,4-tetrahydroisoquinoline derivatives represented by the following general formula as the compounds having a cardiac rate lowering effect (WO 98/13364).

3

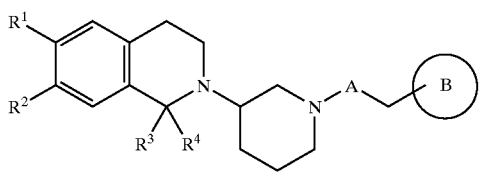

(As to the symbols in the formula, refer to the above-mentioned patent.)

DISCLOSURE OF THE INVENTION

The present inventors have carried out intensive investigations for the drugs which inhibit the $I_f$ current. As a result, it has been found that isoquinoline derivatives represented by the following general formula (I) inhibit the $I_f$ current and have a cardiac rate lowering effect in the heart and confirmed that the derivatives are not accompanied by serious side effects such as convulsion, leading to completion of the present invention.

Specifically, the present invention relates to an isoquinoline derivative represented by the following general formula (I) or a salt thereof and also to drugs, particularly a $I_f$ current inhibitor or, more particularly, a cardiac rate lowering agent, a therapeutic agent for cardiac insufficiency and a therapeutic agent for arrhythmia, containing the derivative or its salt as an effective ingredient.

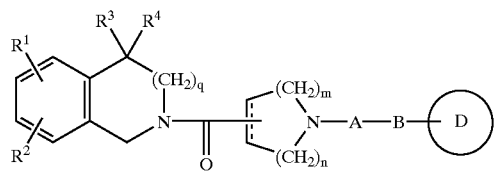

(I)

(The symbols in the above formula have the following meanings:

A: lower alkylene;
B: —C(=O)—NR$^5$— or —NR$^5$—C(=O)—;
R$^1$ and R$^2$: hydrogen atom, lower alkyl or —O-lower alkyl, which may be the same or different;
R$^3$, R$^4$ and R$^5$: hydrogen atom or lower alkyl, which may be the same or different;
ring D: optionally substituted hydrocarbon ring or optionally substituted hetero ring;
m: 1, 2 or 3;
n: 0 or 1; and
q: 1 or 2.)

The compounds of the present invention have a characteristic feature that an amide moiety is always available in the structural formula and have an excellent profile that they exhibit a strong $I_f$ current inhibitory effect without side effects such as convulsion.

As hereunder, the compound (I) of the present invention will be illustrated in detail.

In the definition for the general formula of the present invention, the term "lower" means a linear or branched carbon chain having 1 to 6 carbon atoms unless otherwise mentioned.

As to the "lower alkyl", preferred one is a lower alkyl having 1 to 4 carbon atoms, and more preferably, methyl, ethyl, propyl or isopropyl. As to the "lower alkylene", the preferred one is methylene, ethylene, propylene or methylmethylene.

4

In the formula,

is preferably

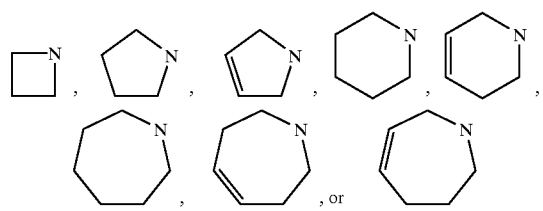

Among them, six-membered ones are particularly preferred.

The "hydrocarbon ring" is a saturated or unsaturated, monocyclic or fused hydrocarbon ring, and "aryl" or "cycloalkyl" is exemplified, with the "aryl" being particularly preferred.

The "aryl" is preferably an aryl having 6 to 14 carbon atoms, including a dihydro group, a tetrahydro group, a hexahydrogroup, etc. where hydrogen atoms are added to arbitrary carbon atoms of the aryl. More preferably, it is phenyl or naphthalene.

The "hetero ring" means a hetero aryl or a saturated hetero ring containing 1 to 4 hetero atoms comprising oxygen, sulfur or nitrogen atoms. Examples of the hetero aryl are a 5- or 6-membered monocyclic hetero aryl (furyl, thienyl, thiazolyl, isothiazolyl, oxazolyl, isoxazolyl, thiadiazolyl, pyridyl, pyrimidinyl, pyrazyl, etc.) and a bicyclic hetero aryl where two 5- or 6-membered hetero aryls are fused (naphthylidinyl, benzylfuranyl, indolyl, benzimidazolyl, benzothiadiazolyl, benzoxazinyl, benzothiazolyl, pyridoindolyl, etc.) although not limited those examples. As to the saturated hetero ring, 5- to 7-membered rings are preferred, and piperidyl and piperazinyl are particularly preferred.

With regard to the "substituent" for the "optionally substituted hydrocarbon ring" or "optionally substituted hetero ring", any group will do so far as it is a group which is usually able to be substituted to such a ring. Preferred examples are halogen atom (F, Cl, Br, I), lower alkyl, lower alkenyl (vinyl, etc.), lower alkynyl (ethynyl, etc.), —OH, —SH, halogeno lower alkyl (trifluoromethyl, etc.), —O-halogeno lower alkyl, —O-lower alkyl, —S-lower alkyl, —CO—O-lower alkyl, —O-lower alkenyl-CO—O-lower alkyl, —COOH, —SO$_2$-lower alkyl, —SO-lower alkyl, —CO-lower alkyl, —CO—NH$_2$, —CO—NH-lower alkyl, —CO—N(lower alkyl)$_2$, —NO$_2$, —CN, —NH$_2$, —NH-lower alkyl, —N(lower alkyl)$_2$, —O-lower alkylene-O—, —NH—CO-lower alkyl and ketone (=O). The substitution may be done with 1 to 5, and preferably, 1 to 3 substituents.

The compound (I) of the present invention has at least one asymmetric carbon atom and, because of that, there are optical isomers such as (R)-compounds, (S)-compounds, etc., racemates, diastereomers and the like. In addition, there is a geometrical isomer or a tautomer depending upon the type of the substituent. The present invention includes all of those separated isomers or a mixture thereof.

The compound (I) of the present invention may form a salt with an acid. Examples of such salt are acid addition salts with a mineral acid such as hydrochloric acid, hydrobromic acid, hydroiodic acid, sulfuric acid, nitric acid and phosphoric acid and with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid and glutamic acid. The present invention further includes a hydrate, a solvate with ethanol, etc. and a polymorph of the compound (I) of the present invention.

The compound of the present invention still further includes all of the so-called prodrugs which are metabolized in vivo and converted to a compound having the above-mentioned general formula (I) or a salt thereof. With regard to a group which forms the prodrug of the compound of the present invention, the groups which are described in *Prog. Med.*, 5:2157–2161(1985) and the groups which are described on pages 163–198, Vol. 7 "Molecular Design" in "*Iyakuhin no Kaihatsu*", published by Hirokawa Shoten in 1990 may be exemplified.

(Preparation Method)

The compound (I) of the present invention may be prepared by utilizing various preparation methods. As hereunder, representative preparation methods will be illustrated.

First Preparation Method

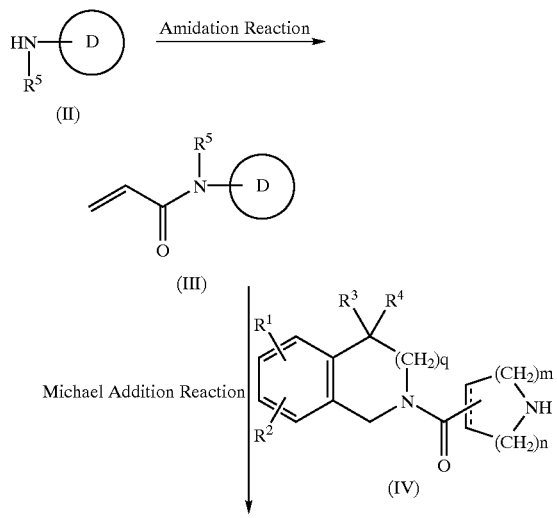

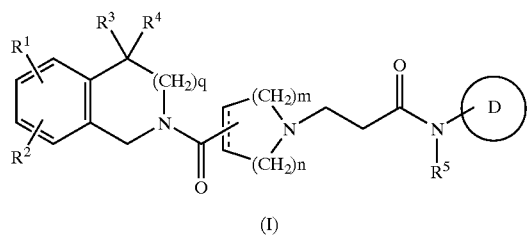

(In the formulae, $R^1$, $R^2$, $R^3$, $R^4$, $R^5$, m, n, q and ring D have the meanings as defined already.)

This preparation method is a method where an amino compound (II) is subjected to an amidation reaction using acrylic acid to give a compound (III), which is then subjected to a Michael addition reaction to a cyclic amino compound (IV) to give a compound (I) of the present invention.

In the amidation reaction, it is possible to use acid halides such as acid chloride and acid bromide, acid azides, activated esters with N-hydroxybenzotriazole (HOBT), p-nitrophenol and N-hydroxysuccinimide, etc., dicyclohexylcarbodiimide (DCC), carbodiimidazole (CDI) and other condensing agent. The Michael addition reaction may be carried out, for example, with ice-cooling, at room temperature or under the condition with heating in a solvent such as toluene, benzene, tetrahydrofuran, dichloroethane, alcohols or dioxane. It is also possible to add an additive such as triethylamine, Triton B, potassium hydroxide, etc.

Second Preparation Method

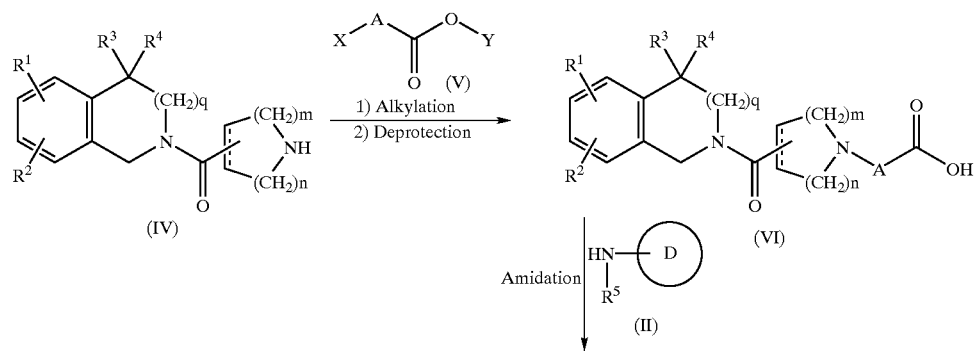

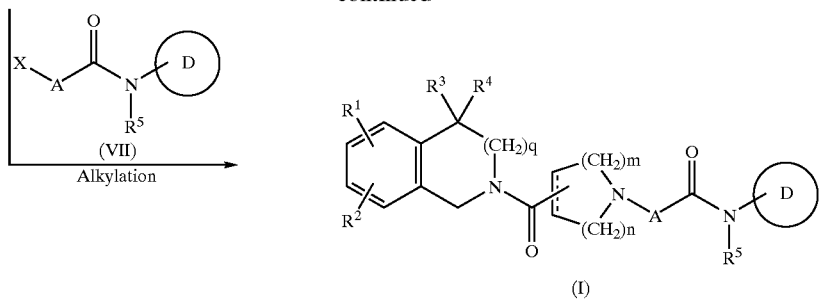

(In the formulae, $R^1$, $R^2$, $R^3$, $R^4$, $R^5$, A, m, n, q and ring D have the meanings as defined already; X is a leaving group; and Y is a protective group.)

This preparation method is a method where a cyclic amino compound (IV) is subjected to a conventional alkylation reaction using a compound (V), followed by deprotecting the protective group of the carboxylic acid to give a compound (VI), which is then conducted with an amino compound (II) by a conventional amidation reaction, or the cyclic amino compound (IV) is alkylated with a separately synthesized compound (VII).

Third Preparation Method

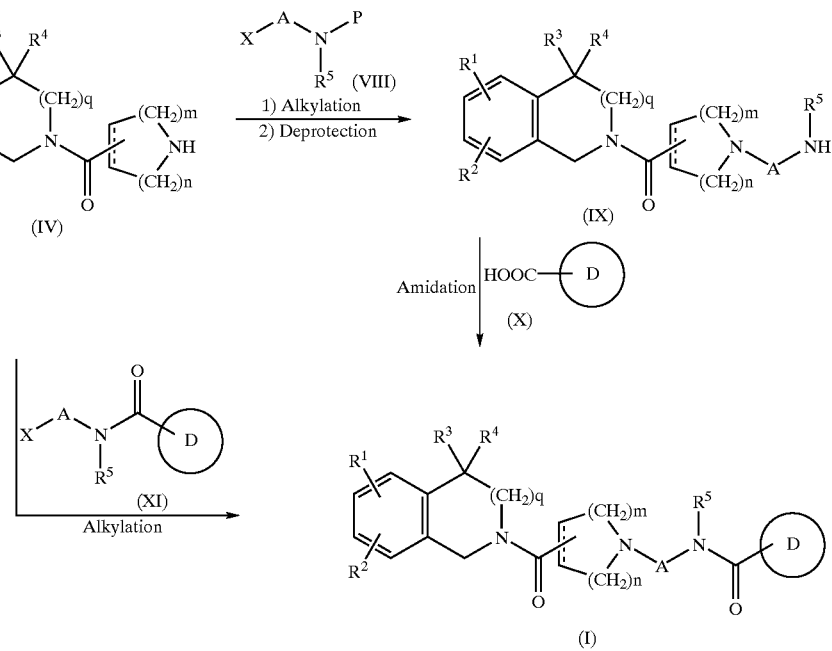

(In the formulae, $R^1$, $R^2$, $R^3$, $R^4$, $R^5$, A, m, n, q, ring D and X have the meanings as defined already; and P is a protective group.)

This preparation method is a method where a cyclic amino compound (IV) is subjected to a conventional alkylation reaction using a compound (VIII), the protective group of the amino group is deprotected to give a compound (IX), which is then conducted with a carboxylic acid (X) or a derivative thereof, or a method where the cyclic amino compound (IV) is alkylated with a separately synthesized compound (XI).

Fourth Preparation Method

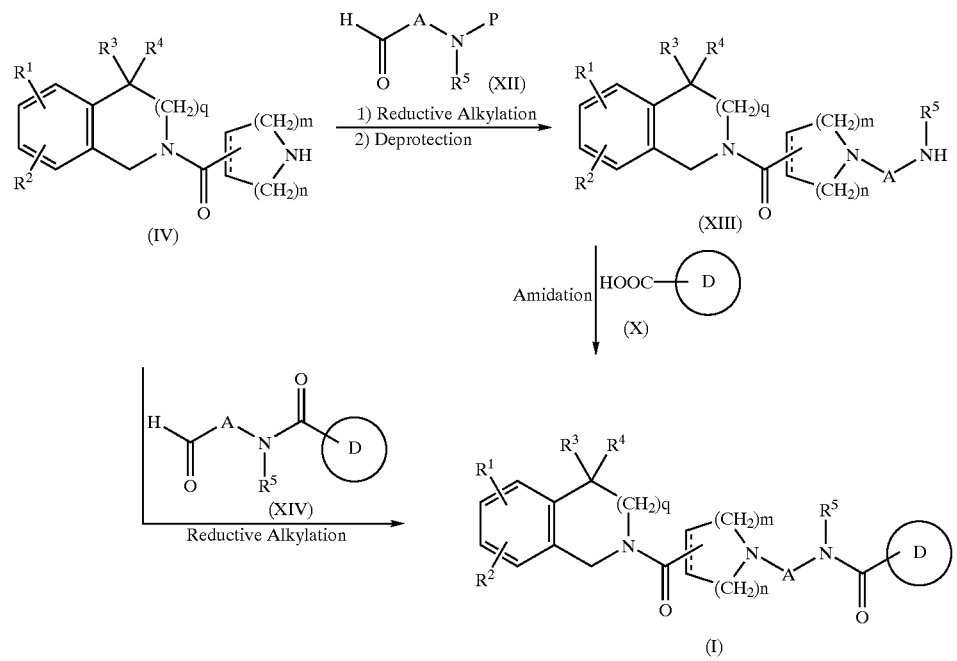

(In the formulae, $R^1$, $R^2$, $R^3$, $R^4$, $R^5$, A, P, m, n, q, ring D and X have the meanings as defined already.)

This preparation method is a method where a cyclic amino compound (IV) is subjected to a conventional reductive alkylation reaction using a compound (XII), followed by deprotecting the protective group of the amino group to give a compound (XIII), which is then conducted with a carboxylic acid (X) or a derivative thereof by a conventional amidation reaction, or a method where the cyclic amino compound (IV) is subjected to a conventional reductive alkylation reaction using a separately synthesized compound (XIV). The reductive alkylation reaction is a method where the cyclic amino compound (IV) is reacted with the compound (XII) or the compound (XIV), and the resulting Schiff base is reduced after being isolated or without being isolated. The reduction may be carried out by reaction upon addition of a reducing agent such as a metal hydride complex (sodium borohydride, lithium borohydride, sodium cyanoborohydride, sodium triacetoxyborohydride, etc.) or borane, or by hydrogenation.

The reaction product prepared by each of the above-mentioned preparation methods is isolated and purified as a liberated compound or a salt, or various solvates such as a hydrate thereof. The salt can be prepared by a usual salt-preparation treatment.

The separation and purification are carried out by applying a usual chemical operation such as extraction, concentration, evaporation, crystallization, filtration, recrystallization and various chromatographic means.

Various isomers can be separated by customary methods utilizing physico-chemical differences among the isomers, and optical isomers can be separated by a usual racemic resolution such as fractional crystallization or chromatography. The optical isomer can also be synthesized from an appropriate optically active starting material.

With regard to the fractional crystallization, fractional crystallization using an optically active organic acid such as tartaric acid derivatives, mandelic acid derivatives and camphorsulfonic acid derivatives may be appropriately carried out. As the solvent, those with which optical resolution is efficiently carried out are appropriately selected.

INDUSTRIAL APPLICABILITY

The compounds of the present invention have an effect of inhibiting the $I_f$ current and exhibit a strong and specific activity of selectively lowering the cardiac rate and reducing the oxygen consumption of cardiac muscle, whereby they are useful as preventive and therapeutic agents for ischemic cardiac diseases such as angina and cardiac infarction and for circulatory diseases such as congestive cardiac insufficiency and arrhythmia.

The compounds of the present invention are particularly highly useful for prevention and therapy of various clinical symptoms caused by the imbalance between supply and consumption of cardiac muscle oxygen such as pectoral angina, cardiac infarction and arrhythmia accompanied therewith and for prevention and therapy of arrhythmia, particularly supraventricular arrhythmia.

In addition, the compounds of the present invention are expected to have an effect of reducing the complications of atherosclerosis, particularly coronary atherosclerosis, by restricting the vascular hemodynamics compression. Further, the compounds of the present invention suppress an excessively increased cardiac rate and are a drug useful in controlling the cardiac rate to a constant state during the general surgical operation, etc.

Since the compounds of the present invention directly act on the $I_f$ current in the above-mentioned cardiac rate lowering effect, it has been confirmed that they have no suppressive effect on atrioventricular conduction and systolic function and have a high selectivity to a cardiac rate lowering effect to visual hindrance. With regard to the ion current contributing in the formation of action potential in heart, it has been known that the current which permeates Na channel, K channel and Ca channel is present besides the $I_f$ current. However, since the compounds of the present invention do not show a significant inhibitory effect to the above-mentioned ion current existing in heart other than the $I_f$ current at a dose by which the $I_f$ current is inhibited, it is also expected that the compounds have less side effects caused by inhibition of the current other than the $I_f$ current. Further, the compounds of the present invention are not accompanied by serious side effects such as convulsion. Accordingly, the compounds of the present invention are useful for prevention and therapy of the above-mentioned various diseases as a cardiac rate lowering agent having less side effects. The compounds of the present invention are furthermore useful as a suppressor for ectopic automatism acceleration or triggered activity caused by the $I_f$ current in some symptoms such as cardiac infarction and hypertension.

Since the compounds of the present invention lower the cardiac rate by inhibiting the $I_f$ current, they are also useful as therapeutic agents for cardiac insufficiency and for arrhythmia.

Pharmacological effects of the compounds of the present invention were confirmed according to the following test methods.

(Test Methods)

1. Test on Inhibition of $I_f$ Current

Test on inhibition of $I_f$ current was carried out by a method according to Robert, E., et al., *Br. J. Pharmacol.*, 110:343–349, 1993.

<Isolation of Cardiac Muscle>

Male guinea pigs of a Hartley strain having a body weight of about 200 to 400 g were fainted away by knocking the head, and then a heart was quickly excised under bleeding by cutting the carotid artery. The heart was transferred to a Tyrode's solution which was fully aerated with a mixed gas of 95% oxygen and 5% carbon dioxide gas and a sinoatrial node (pacemaker) site (about 3×5 mm) was cut out. The cut-out sinoatrial node was subjected to an enzymatic treatment at 37° C. for about 30 minutes in a $Ca^{2+}$-free Tyrode's solution containing collagenase (1.5 mg/ml) (manufactured by Yakult Honsha Co., Ltd.). Thereafter, it was allowed to stand at 4° C. for 1 hour or more in a $K^+$ rich solution (KB recovery solution). The sinoatrial node site after the treatment was minced with an injection needle and subjected to pipetting to give isolated cardiac muscle cells.

<Measurement of Current>

The resulting isolated cardiac muscle was scattered in a chamber for exclusive use, and a patch clamp method (a whole cell mode) was applied to the spindle-shaped cells carrying out a spontaneous contraction. The holding potential was made −40 mV and, a hyperpolarization pulse (for 1 second) was successively applied from this potential to −10, −20, −30, . . . and −80 mV, to induce the $I_f$ current. The $I_f$ current at the hyperpolarization pulse of −80 mV was biggest, and therefore, with regard to the evaluation of the pharmacological effect, an effect of the test compound to the $I_f$ current induced by the pulse of −80 mV was evaluated.

<Evaluation of Pharmacological Effect>

An extracellular solution(Tyrode's solution) containing the test compound was started to be perfused and, with intervals of 5 seconds each, the $I_f$ current was induced by a hyperpolarization pulse of −80 mV and was recorded until about 100th pulse (for about 8 minutes). An effect of the drug was confirmed to become in a saturated state at 90 pulses or more. With regard to the $I_f$ current inhibitory effect of the test compound, each of the $I_f$ currents obtained before the perfusion and after the 90th pulse was measured, and the comparison was made in terms of the concentration ($IC_{50}$) of the substance inhibiting the $I_f$ current to an extent of 50%.

The result was that the $IC_{50}$ value of the compounds of the Examples of the present invention was $10^{-8}$ M to $10^{-5}$ M.

2. Test on Cardiac Rate Lowering Effect

The test on cardiac rate lowering effect was carried out by a method according to Walter, K., et al. *Eur. J. Pharmacol.*, 104(1–2):9–18, 1984.

Male guinea pigs of a Hartley strain having a body weight of about 250 to 400 g were fainted away by knocking the head and killed by draining out the blood, and the heart was excised. A right atrium sample was prepared in a Tyrode's solution which was fully aerated with 95% oxygen and 5% carbon dioxide gas. The sample was applied to a hook made of stainless steel and suspended at a load tension of 1.0 g in a Magnus tube filled with a Tyrode's solution which was well aerated with 95% oxygen and 5% carbon dioxide gas, whereby the spontaneously pulsing cardiac rate was recorded. After suspending, the sample was allowed to stand for a stabilization period of 1 hour or more, the test compound was cumulatively added into a Magnus tube every 30 to 45 minutes and a concentration vs. effect curve was determined from the data after 30 minutes from the administration of the substance, whereby the effect was judged. The cardiac rate lowering effect was compared in terms of the concentration ($EC_{30}$) of the substance which lowered the spontaneous cardiac rate to an extent of 30% from the data before the administration. The result was that the compounds of the present invention showed a strong cardiac rate lowering effect. The result of the tests is shown in Table A.

TABLE A

| Compound of the Present Invention | Cardiac Rate Lowering Effect ($EC_{30}$ μM) |
|---|---|
| Example 2 | 0.30 |
| Example 4 | 0.57 |
| Example 5 | 0.38 |
| Example 6 | 0.32 |
| Example 9 | 0.27 |
| Example 10 | 0.27 |
| Example 12 | 0.27 |
| Example 14 | 0.47 |
| Example 26 | 0.24 |
| Example 27 | 0.41 |
| Example 29 | 0.29 |
| Example 37 | 0.30 |
| Example 38 | 0.29 |
| Example 40 | 0.33 |
| Example 49 | 0.29 |
| Example 50 | 0.31 |

3. Test on Convulsion Expression

Male rats of a Wister strain having a body weight of 250 to 350 g under awaking were fixed in a cage, and the test compound was administered from a tail vein. The test compound was administered at a dose of either 20 mg/kg (i.v.) or 40 mg/kg (i.v.) once for each rat. After administration of the test compound, behavior of the animal was observed for about 1 hour without restraint. The influence of the test compound on the spontaneous behavior of the rat was evaluated by the fact whether or not the convulsion was noted within the observed period.

The result was that there were compounds showing no convulsion-inducing effect even by an intravenous administration of 40 mg/kg while the compound of Example 8 of Japanese Patent Laid-Open No. 138172/1990 and the compounds of Examples 24 and 33 of WO 98/13364 cited in the Background of the Invention showed a convulsion-inducing effect at a dose of 20 mg/kg which was one half of the above (Table B).

TABLE B

| Compounds of the Examples of the Present Invention and Control Compounds | Dose | General Findings |
|---|---|---|
| Example 2 | 40 mg/kg | No abnormal finding |
| Example 4 | 40 mg/kg | No abnormal finding |
| Example 5 | 40 mg/kg | No abnormal finding |
| Example 6 | 40 mg/kg | No abnormal finding |
| Example 9 | 40 mg/kg | No abnormal finding |
| Example 10 | 40 mg/kg | No abnormal finding |
| Example 14 | 40 mg/kg | No abnormal finding |
| Example 26 | 40 mg/kg | No abnormal finding |
| Example 27 | 40 mg/kg | No abnormal finding |
| Example 28 | 40 mg/kg | No abnormal finding |
| Example 29 | 40 mg/kg | No abnormal finding |
| Example 30 | 40 mg/kg | No abnormal finding |
| Example 37 | 40 mg/kg | No abnormal finding |
| Example 38 | 40 mg/kg | No abnormal finding |
| Example 40 | 40 mg/kg | No abnormal finding |
| Example 47 | 40 mg/kg | No abnormal finding |
| Example 49 | 40 mg/kg | No abnormal finding |
| Example 50 | 40 mg/kg | No abnormal finding |
| Example 8 of JP Laid-Open 138172/1990 (Control Compound) | 20 mg/kg | Convulsion |
| Example 24 of WO 98/13364 (Control Compound) | 20 mg/kg | Convulsion |
| Example 33 of WO 98/13364 (Control Compound) | 20 mg/kg | Convulsion |

From the above result, it is now apparent that, when an amide moiety which is a structural characteristic of the compounds of the present invention is introduced, the compounds of the present invention do not show an convulsion-inducing effect but effectively inhibit the $I_f$ current showing a cardiac rate lowering effect.

A pharmaceutical composition containing one, two or more of the compounds of the present invention or salts thereof are prepared using a usual pharmaceutically acceptable carrier.

Administration of the pharmaceutical composition in the present invention may be any route of oral administration and parenteral administration such as by means of injection agents, suppositories, percutaneous agents, inhalation agents or vesicoclysis.

The dose may be appropriately decided for each case taking into consideration symptom, age and sex of the subject, etc. and, in the case of oral administration, it is usually about 0.1 mg/kg to 100 mg/kg per day for an adult. The administration is effected at once or by dividing into 2 to 4 times a day. In the case of an intravenous injection which is carried out depending upon the symptom, it is usually about 0.01 mg/kg to 10 mg/kg per day for an adult. The administration is effected at once or by dividing into one to several times a day.

With regard to a carrier for the pharmaceutical preparation, solid or liquid nontoxic substances for drugs may be exemplified.

With regard to a solid composition for oral administration according to the present invention, there are used tablets, pills, capsules, diluted powder, granules, etc. In such solid compositions, one or more active ingredients are mixed with at least one inert diluent such as lactose, mannitol, glucose, hydroxypropyl cellulose, microcrystalline cellulose, starch, polyvinylpyrrolidone, agar, pectin or magnesium metasilicate aluminate. The composition may contain additives other than the inert diluent, for example, lubricants such as magnesium stearate, disintegrating agents such as calcium cellulose glycolate, stabilizers such as lactose and solubilization aids such as glutamic acid or aspartic acid according to a conventional method. If necessary, tablets or pills may be coated with sugar coats such as sucrose, gelatin, hydroxypropyl cellulose or hydroxypropylmethyl cellulose phthalate or with films which are soluble in stomach or in intestine.

The liquid composition for oral administration includes a pharmaceutically acceptable emulsion, solution, suspension, syrup, elixir or the like, or a commonly used inert diluent such as purified water or ethanol. Besides the inert diluent, the composition may further contain auxiliary agents such as moisturizers and suspending agents, sweeteners, flavors, fragrances or antiseptics.

The injection solution for a parenteral administration includes aseptic aqueous or non-aqueous solutions, suspensions and emulsions. The aqueous solutions and suspensions contain, for example, distilled water for injection and physiological saline. Examples of the non-aqueous solutions and suspensions are ethylene glycol, propylene glycol, polyethylene glycol, vegetable oils such as cacao butter, olive oil and sesame oil, alcohols such as ethanol, gum arabic and Polysolvate 80 (trade name). Such composition may further contain additives such as isotonizing agents, antiseptics, moisturizers, emulsifiers, dispersing agents, stabilizers (such as lactose), and solubilization aids (such as glutamic acid or aspartic acid). They may be asepticized, for example, by filtration through a bacteria-keeping filter, by compounding with a bactericide, or by irradiation. They may also be used in such a manner that an aseptic solid composition is prepared, and then, before use, the composition is dissolved in an aseptic water or in an aseptic solvent for injection.

BEST MODE FOR CARRYING OUT THE INVENTION

Hereunder, the desired compounds of the present invention and the preparation methods thereof will be further illustrated by way of the Examples although the present invention is never limited by those Examples. Incidentally, methods for the preparation of the starting compounds for the compounds of the present invention will be mentioned in the Referential Examples.

Referential Example 1

A conventional acylation reaction was carried out using a tetrahydrofuran solution (30 ml) of 4.6 g of 3,4-dimethoxyaniline, 5.0 ml of triethylamine and 2.68 ml of acryloyl chloride to give 5.22 g of 3,4-dimethoxyacrylanilide as white crystals.

The compounds of Referential Examples 1-1 to 1-9 were synthesized by the same manner as in Referential Example 1 (see Table 1 shown later).

Referential Example 2

A conventional amidation reaction was carried out using a dichloromethane solution (40 ml) of 2.53 g of (±)-6,7-dimethoxy-1,2,3,4-tetrahydroisoquinoline, 3.0 g of N-(tert-butyloxycarbonyl)nipecotic acid, 3.0 g of 1-ethyl-3-[3-(dimethylamino)propyl]carbodiimide hydrochloride and 0.89 g of 1-hydroxybenztriazole to give 3.77 g of (±)-6,7-dimethoxy-2-{[1-(tert-butyloxycarbonyl)-3-piperidyl]carbonyl}-1,2,3,4-tetrahydroisoquinoline. Deprotection of 3.77 g of (±)-6,7-dimethoxy-2-{[1-(tert-butyloxycarbonyl)-3-piperidyl]carbonyl}-1,2,3,4-tetrahydroisoquinoline was further carried out using 10 ml of an ethyl acetate solution containing 4N hydrochloric acid to give 2.30 g of (±)-6,7-dimethoxy-2-[(3-piperidyl)carbonyl]-1,2,3,4-tetrahydroisoquinoline hydrochloride as colorless crystals.

The compounds of Referential Examples 2-1 to 2-11 were synthesized by the same manner as in Referential Example 2 (see Table 1 shown later).

Referential Example 3

(±)-6,7-Dimethoxy-2-[(3-piperidyl)carbonyl]-1,2,3,4-tetrahydroisoqinoline hydrochloride (3.19 g) was desalted by a customary method, and a conventional alkylation reaction was carried out using an acetonitrile solution (30 ml) of the residue, 2.85 g of N-(2-bromoethyl)phthalimide and 1.55 g of potassium carbonate to give 3.83 g of (±)-6,7-dimethoxy-2-{[3-(2-phthalimidoethyl)piperidyl]carbonyl}-1,2,3,4-tetrahydroisoquinoline. Then, 3.83 g of (±)-6,7-dimethoxy-2-{[3-(2-phthalimidoethyl)piperidyl]carbonyl}-1,2,3,4-tetrahydroisoquinoline was deprotected by a customary method using 45 ml of a methanolic solution containing 40% of methylamine to give 2.67 g of (±)-2-{[3-(2-aminoethyl)piperidyl]carbonyl}-6,7-dimethoxy-1,2,3,4-tetrahydroisoquinoline as a yellow foamy substance.

The compounds of Referential Examples 3-1 to 3-4 were synthesized by the same manner as in Referential Example 3 (see Table 1 shown later).

Referential Example 4

A conventional alkylation reaction was carried out using a dimethylformamide solution (10 ml) of 1.77 g of 2-(3,4-dimethoxyphenyl)acetonitrile, 1.00 g of sodium hydride and 4.26 g of methyl iodide to give 1.78 g of 2-(3,4-dimethoxyphenyl)-2-methylpropionitrile. A conventional catalytic hydrogenation reaction was carried out using an ethanolic solution (30 ml) of 1.75 g of 2-(3,4-dimethoxyphenyl)-2-methylpropionitrile, 3.0 ml of an aqueous 28% ammonia solution and 4.3 g of Raney nickel to give 1.59 g of 2-(3,4-dimethoxyphenyl)-2-methylpropylamine. Then, a conventional cyclization reaction was carried out using a formic acid solution (8 ml) of 1.58 g of 2-(3,4-dimethoxyphenyl)-2-methylpropylamine and 0.252 g of paraformaldehyde to give 1.34 g of 6,7-dimethoxy-4,4-dimethyl-1,2,3,4-tetrahydroisoquinoline as a pale yellow oily substance. A conventional alkylation reaction was carried out using a solution (10 ml) of 1.77 g of 2-(3,4-dimethoxyphenyl)acetonitrile in dimethylformamide, 1.00 g of sodium hydride and 4.26 g of methyl iodide to give 1.78 g of 2-(3,4-dimethoxyphenyl)-2-methylpropionitrile.

EXAMPLE 1

A toluene suspension (3 ml) of 0.268 g of (±)-6,7-dimethoxy-2-[(3-piperidyl)carbonyl]-1,2,3,4-tetrahydroisoquinoline and 0.166 g of 3,4-dimethylacrylanilide was stirred overnight under heating to reflux. The reaction solution was evaporated off in vacuo, and a 1N aqueous sodium hydroxide solution was added to the residue to make it basic, followed by extracting with chloroform. The organic layer was dried over anhydrous magnesium sulfate. The drying agent was filtered off, the filtrate was concentrated in vacuo, and the residue was purified by silica gel column chromatography (chloroform:methanol=100:4). To a ethyl acetate solution (8 ml) of the resulting oily substance was added an ethyl acetate solution (0.227 ml) containing 4N hydrochloric acid, and the solvent was evaporated off in vacuo. The residue was crystallized from ethyl acetate-ethanol to give 0.337 g of (±)-3-[3-(6,7-dimethoxy-1,2,3,4-tetrahydroisoquinoline-2-carbonyl)piperidino]-N-(3,4-dimethoxyphenyl)propanamide hydrochloride as colorless crystals.

EXAMPLE 2

Using 3.35 g of (±)-6,7-dimethoxy-2-[(3-piperidyl)carbonyl]-1,2,3,4-tetrahydroisoquinoline and 1.91 g of 3,4-methylenedioxyacrylanilide, the same operation as in Example 1 was carried out to give 4.95 g of (±)-3-[3-(6,7-dimethoxy-1,2,3,4-tetrahydroisoquinoline-2-carbonyl)piperidino]-N-(3,4-methylenedioxyphenyl)propanamide hydrochloride as colorless crystals.

EXAMPLE 3

Using 0.264 g of (±)-6,7-dimethoxy-2-[(3-piperidyl)carbonyl]-1,2,3,4-tetrahydroisoquinoline and 0.150 g of 3,5-dimethoxyacrylanilide, the same operation as in Example 1 was carried out to give 0.243 g of (±)-3-[3-(6,7-dimethoxy-1,2,3,4-tetrahydroisoquinoline-2-carbonyl)piperidino]-N-(3,5-dimethoxyphenyl)propanamide 1/2 oxalate as colorless crystals.

EXAMPLE 4

Using 0.270 g of (±)-6,7-dimethoxy-2-[(3-piperidyl)carbonyl]-1,2,3,4-tetrahydroisoquinoline and 0.132 g of 4-methoxyacrylanilide, the same operation as in Example 1 was carried out to give 0.281 g of (±)-3-[3-(6,7-dimethoxy-1,2,3,4-tetrahydroisoquinoline-2-carbonyl)piperidino]-N-(4-methoxyphenyl)propanamide hydrochloride as colorless crystals.

EXAMPLE 5

Using 7.80 g of (R)-6,7-dimethoxy-2-[(3-piperidyl)carbonyl]-1,2,3,4-tetrahydroisoquinoline and 3.66 g of 3,4-methylenedioxyacrylanilide, the same operation as in Example 1 was carried out to give 11.2 g of (−)-3-[(R)-3-(6,7-dimethoxy-1,2,3,4-tetrahydroisoquinoline-2-carbonyl)piperidino]-N-(3,4-methylenedioxyphenyl)propanamide L-tartrate as colorless crystals.

EXAMPLE 6

Using 10.9 g of (S)-6,7-dimethoxy-2-[(3-piperidyl)carbonyl]-1,2,3,4-tetrahydroisoquinoline and 5.24 g of 3,4-methylenedioxyacrylanilide, the same operation as in Example 1 was carried out to give 15.6 g of (+)-3-[(S)-3-(6,7-dimethoxy-1,2,3,4-tetrahydroisoquinoline-2-carbonyl)piperidino]-N-(3,4-methylenedioxyphenyl)propanamide D-tartrate as colorless crystals.

EXAMPLE 7

To 0.65 g of (±)-6,7-dimethoxy-2-[(3-piperidyl)carbonyl]-1,2,3,4-tetrahydroisoquinoline hydrochloride was added a 1N aqueous sodium hydroxide solution to make it basic, followed by extracting with chloroform. The organic layer was dried over anhydrous magnesium sulfate, the solvent was evaporated off in vacuo, and the residue was dissolved in acetonitrile (20 ml). To this were added 0.32 ml of ethyl 4-bromobutyrate and 0.32 g of potassium carbonate, followed by stirring at 80° C. for 8 hours. The reaction solution was cooled to room temperature, the solvent was evaporated off in vacuo, and the residue was extracted with chloroform. The organic layer was washed with a saturated sodium chloride solution and dried over anhydrous magnesium sulfate. The drying agent was filtered off, the filtrate was concentrated in vacuo, and the residue was purified by silica gel column chromatography (chloroform:methanol=97:3). 3.7 ml of a 1N aqueous sodium hydroxide solution was added to a ethanol solution (7 ml) of the resulting oily substance (0.78 g), and the mixture was stirred at room temperature for 3 hours. After neutralizing with 1N hydrochloric acid, the reaction solution was evaporated off in vacuo, and the residue was subjected to azeotropy with toluene twice. To a mixed solution of the residue and 0.24 g of 3,4-methylenedioxyaniline in tetrahydrofuran (8 ml) and DMF (8 ml) were added 0.37 g of 1-ethyl-3-[3-(dimethylamino)propyl]carbodiimide hydrochloride and 0.12 g of 1-hydroxybenztriazole, followed by stirring overnight at room temperature. The reaction solution was evaporated off in vacuo, a 1N aqueous sodium hydroxide solution was added to the residue to make it basic, followed by extracting with chloroform. The organic layer was dried over anhydrous magnesium sulfate. The drying agent was filtered off, the filtrate was concentrated in vacuo, and the residue was purified by silica gel column chromatography (chloroform:methanol=93:7). To a solution of the residue in methanol was added 0.12 g of oxalic acid to give an oxalate, which was then crystallized from a mixed solvent of ethyl acetate and methanol to give 0.50 g of (±)-4-[3-(6,7-dimethoxy-1,2,3,4-tetrahydroisoquinoline-2-carbonoyl)piperidino]-N-(3,4-methylenedioxyphenyl)butanamide oxalate as colorless crystals.

EXAMPLE 8

Using 0.69 g of (±)-2-[(3-piperidyl)carbonyl]-6,7-dimethoxy-1,2,3,4-tetrahydroisoquinoline hydrochloride and 0.27 ml of ethyl bromoacetate, the same operation as in Example 7 was carried out to give 0.04 g of (±)-2-[3-(6,7-dimethoxy-1,2,3,4-tetrahydroisoquinoline-2-carbonyl)piperidino]-N-(3,4-methylenedioxyphenyl)ethanamide oxalate as colorless crystals.

EXAMPLE 9

To a solution of 0.410 g of (±)-2-{[3-(2-aminoethyl)piperidyl]carbonyl}-6,7-dimethoxy-1,2,3,4-tetrahydroisoquinoline in tetrahydrofuran (10 ml) were added 0.220 g of piperonylic acid, 0.300 g of 1-ethyl-3-[3-(dimethylamino)propyl]carbodiimide hydrochloride and 0.090 g of 1-hydroxybenztriazole, followed by stirring overnight at room temperature. The reaction solution was evaporated off in vacuo, and a 1N aqueous sodium hydroxide solution was added to the residue to make it basic, followed by extracting with chloroform. The organic layer was dried over anhydrous magnesium sulfate. The drying agent was filtered off, the filtrate was concentrated in vacuo, and the residue was purified by silica gel column chromatography (chloroform:methanol=50:1). Then, 0.40 ml of an ethyl acetate solution containing 4N hydrochloric acid was added to a solution of the residue in ethanol to give a hydrochloride. This was crystallized from acetone to give 0.240 g of (±)-N-{2-[3-(6,7-dimethoxy-1,2,3,4-tetrahydrolsoquinoline-2-carbonyl)piperidino]ethyl}-3,4-methylenedioxybenzamide hydrochloride as colorless crystals.

EXAMPLE 10

Using 0.500 g of (±)-2-{[3-(2-aminoethyl)piperidyl]carbonyl}-6,7-dimethoxy-1,2,3,4-tetrahydroiso quinoline and 0.330 g of 3-methoxybenzoic acid, the same operation as in Example 9 was carried out to give 0.437 g of (±)-N-{2-[3-(6,7-dimethoxy-1,2,3,4-tetrahydroisoquinoline-2-carbonyl)-piperidino]ethyl}-3-methoxybenzamide oxalate as colorless crystals.

EXAMPLE 11

Using 0.720 g of (±)-2-{[3-(2-aminoethyl)piperidyl]carbonyl}-6,7-dimethoxy-1,2,3,4-tetrahydroisoquinoline and 0.380 g of 3,4-dimethoxybenzoic acid, the same operation as in Example 9 was carried out to give 0.520 g of (±)-N-{2-[3-(6,7-dimethoxy-1,2,3,4-tetrahydroisoquinoline-2-carbonyl)-piperidino]ethyl}-3,4-dimethoxybenzamide hydrochloride as colorless crystals.

The compounds of Examples 12 to 25 were synthesized in a similar manner as in Example 1 (see Table 2 shown later).

The compounds of Examples 26 to 51 were synthesized in a similar manner as in Example 9 (see Table 2 shown later).

EXAMPLE 52

To a tetrahydrofuran solution (10 ml)of 0.32 g of N-(3,4-methylenedioxybenzoyl)-N-methylglycine ethyl ester were added dropwise 2.8 ml of diisobutyl aluminum hydride (0.95M hexane solution) at −78° C., and the mixture was stirred in an argon atmosphere at −78° C. for 2 hours. A 1N aqueous ammonium chloride solution (3 ml) was added to the reaction solution, and after returning the temperature to room temperature, the mixture was extracted with ethyl acetate. The organic layer was dried over anhydrous magnesium sulfate. The drying agent was filtered off, and the filtrate was concentrated in vacuo to give crude N-(3,4-methylenedioxybenzoyl)-N-methylglycinal. Triethylamine (0.14 ml) was added to a suspension of 0.34 g of (±)-2-[(3-piperidyl)carbonyl]-6,7-dimethoxy-1,2,3,4-tetrahydroisoquinoline hydrochloride in tetrahydrofuran (5 ml) with ice cooling, and the mixture was stirred for 10 minutes with ice cooling. To the reaction solution were successively added a tetrahydrofuran solution (5 ml) of the crude N-(3,4-methylenedioxybenzoyl)-N-methylglycinal acetic acid (0.057 ml) and sodium triacetoxyborohydride (0.25 g), followed by stirring overnight at room temperature. A 1N aqueous sodium hydroxide solution was added to the reaction solution to make it basic, followed by extracting with chloroform. The organic layer was dried over anhydrous magnesium sulfate. The drying agent was filtered off, the filtrate was concentrated in vacuo, and the residue was purified by silica gel column chromatography (chloroform:methanol=24:1). Then, 0.028 g of oxalic acid was added to a solution of the residue in methanol to give an oxalate. Thus, 0.075 g of (±)-N-{2-[3-(6,7-dimethoxy-1,2,3,4-tetrahydroisoquinoline-2-carbonyl)piperidino]ethyl}-N-methyl-(3,4-methylenedioxy)benzamide oxalate was obtained as a pale yellow amorphous solid.

EXAMPLE 53

To a ethanol solution of 9.32 g of (±)-3-[(S)-3-(6,7-dimethoxy-1,2,3,4-tetrahydroisoquinoline-2-carbonyl)piperidino]-N-(3,4-methylenedioxyphenyl)propanamide was added 2.07 g of fumaric acid, and the mixture was evaporated in vacuo. Thus, 9.38 g of (±)-3-[(S)-3-(6,7-dimethoxy-1,2,3,4-tetrahydroisoquinoline-2-carbonyl)piperidino]-N-(3,4-methylenedioxyphenyl)propanamide fumarate was obtained as colorless crystals from ethanol/2-butanone.

Table 1 shows chemical structural formula and physicochemical properties of the Referential Examples, and Table 2 shows chemical structural formula and physico-chemical properties of the Examples. The compounds whose chemical structural formula are described in Table 3 can be easily prepared in substantially the same manner as described in the above Examples or Preparation Methods, or by applying some modified methods obvious to the persons skilled in the art thereto.

Symbols in the Tables have the following meanings. Rf.: Referential Example; Structure: structure; Data: data; Ex.: Examples; Salt: salt; m.p.: melting point; NMR: nuclear magnetic resonance (TMS being used as an internal standard); [α]$_D$: angle of rotation; OMe: methoxy; OEt: ethoxy; OiPr: isopropoxy; Me: methyl; L-TA: (L)-tartaric acid; D-TA: (D)-tartaric acid; and Fu: fumaric acid.

TABLE 1

| Rf. | Structure | Data | Rf. | Structure | Data |
|---|---|---|---|---|---|
| 1 | acrylamide with 3,4-dimethoxyphenyl | m.p. 106–107° C. | 1-5 | acrylamide with 4-methoxy-3-trifluoromethylphenyl | m.p. 118–120° C. |
| 1-1 | acrylamide with 3,4-methylenedioxyphenyl | m.p. 157–158° C. | 1-6 | acrylamide with benzothiazol-6-yl | m.p. 196–199° C. |
| 1-2 | acrylamide with 3,5-dimethoxyphenyl | m.p. 98–100° C. | 1-7 | acrylamide with 4-methyl-3-methoxyphenyl | m.p. 107–108° C. |
| 1-3 | acrylamide with 4-methoxyphenyl | m.p. 97–98° C. | 1-8 | acrylamide with 4-methyl-3-fluorophenyl | m.p. 167–170° C. |
| 1-4 | acrylamide with 3-chlorophenyl | m.p. 102–105° C. | 1-9 | acrylamide with 6-methoxypyridin-3-yl | m.p. 126–127° C. |
| 2 | 6,7-dimethoxy-1,2,3,4-tetrahydroisoquinoline-2-carbonyl-piperidine HCl | m.p. 235–237° C. | | | |
| 2-1 | 6-methoxy-1,2,3,4-tetrahydroisoquinoline-2-carbonyl-piperidine | $^1$H-NMR(CDCl$_3$): 1.50–1.54(1H, m), 1.71–1.84(3H, m), 2.63–2.92(5H, m), 2.98–3.08(2H, m), 3.70–3.83(2H, m), 3.79(3H, s), 4.62–4.64(2H, m), 6.68(1H, s), 6.77(1H, dd), 7.04(1H, dd). | | | |
| 2-2 | 1,2,3,4-tetrahydroisoquinoline-2-carbonyl-piperidine | $^1$H-NMR(CDCl$_3$): 1.50–1.55(1H, m), 1.64–1.85(3H, m), 2.63–3.08(7H, m), 3.72–3.84(2H, m), 4.68–4.71(2H, m), 7.15–7.23(4H, m). | | | |
| 2-3 | 6,7-dimethoxy-1,2,3,4-tetrahydroisoquinoline-2-carbonyl-piperidine | $^1$H-NMR(CDCl$_3$): 1.50–1.55(1H, m), 1.71–1.85(3H, m), 2.64–2.93(5H, m), 2.98–3.08(2H, m), 3.71–3.83(2H, m), 3.86(6H, s), 4.61–4.65(2H, m), 6.58–6.63(2H, m). | | | |

TABLE 1-continued
| 2-4 | 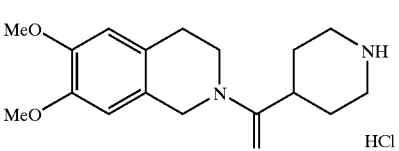 | ¹H-NMR(CDCl₃): 1.50–1.58(1H, m), 1.72–1.85(3H, m), 2.64–2.93(5H, m), 2.99–3.09(2H, m), 3.71–3.83(2H, m), 3.86(6H, s), 4.61–4.65(2H, m), 6.58–6.63(2H, m). |
|---|---|---|
| 2-5 | 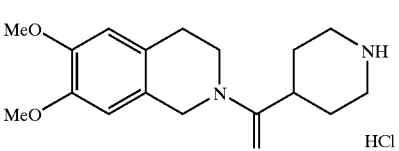 | m.p. 275–286° C. |
| 2-6 | 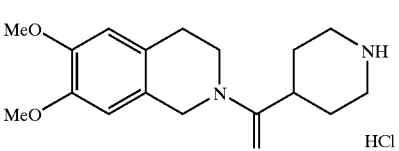 | ¹H-NMR(CDCl₃): 1.45–1.81(6H, m), 2.59–2.95(7H, m), 3.59–3.89(2H, m), 3.85–3.87(6H, m), 4.41–4.61(2H, m), 6.65–6.90(2H, m). |
| 2-7 | 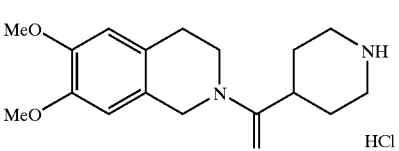 | ¹H-NMR(CDCl₃): 1.64–1.83(3H, m), 2.14–2.19(1H, m), 2.76–2.88(4H, m), 3.16–3.23(1H, m), 3.65–3.99(2H, m), 3.86(3H, s), 3.86(3H, s), 4.51–4.68(2H, m), 6.58–6.63(2H, m). |
| 2-8 | 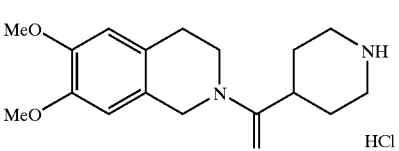 | ¹H-NMR(CDCl₃): 2.19–2.22(2H, m), 2.78–2.82(2H, m), 2.99–3.03(2H, m), 3.54–3.55(2H, m), 3.78–3.82(2H, m), 3.86(6H, s), 4.66(2H, s), 5.98–6.01(1H, m), 6.60–6.62(2H, m). |
| 2-9 | 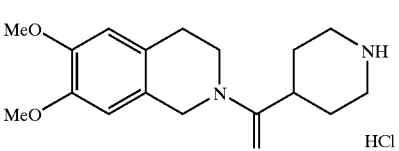 | m.p. 139–141° C. |
| 2-10 | 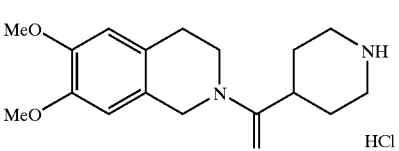 | ¹H-NMR(CDCl₃): 1.93–2.06(2H, m), 2.71–2.89(3H, m), 2.96–3.02(1H, m), 3.09–3.27(3H, m), 3.73–3.77(1H, m), 3.86(3H, s), 3.87(3H, s), 3.80–3.92(1H, m), 4.62–4.66(2H, m), 6.58–6.63(2H, m). |
| 2-11 | 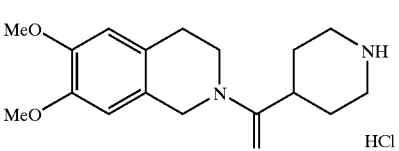 | ¹H-NMR(CDCl₃): 1.24(3H, s), 1.29(3H, s), 1.47–1.60(1H, m), 1.72–1.89(3H, m), 2.64–2.72(1H, m), 2.80–2.93(2H, m), 2.99–3.09(2H, m), 3.47–3.64(2H, m), 3.84–3.87(6H, m), 4.65–4.67(2H, m), 6.53–6.57(1H, m), 6.77–6.80(1H, m). |
| 3 |  | ¹H-NMR(CDCl₃): 1.50–1.72(2H, m), 1.73–1.88(2H, m), 1.98–2.35(5H, m), 2.43–2.53(2H, m), 2.74–2.95(6H, m), 3.65–3.82(2H, m), 3.85(3H, s), 3.86(3H, s), 4.62(2H, d), 6.61–6.63(2H, m). |

TABLE 1-continued

| Ex. | Structure | Data |
|---|---|---|
| 3-1 | (6,7-dimethoxy-1,2,3,4-tetrahydroisoquinolin-2-yl)carbonyl-1,2,3,6-tetrahydropyridine with N-(2-aminoethyl) | ¹H-NMR(CDCl₃): 2.30–2.32(2H, m), 2.55(2H, t), 2.63(2H, t), 2.78–2.87(4H, m), 3.18–3.19(2H, m), 3.18–3.19(2H, m), 3.79–3.82(2H, m), 3.86(6H, s), 4.66(2H, s), 5.94–5.96(1H, m), 6.60–6.62(2H, m). |
| 3-2 | (6,7-dimethoxy-THIQ)carbonyl-azetidine with N-(2-aminoethyl) | ¹H-NMR(CDCl₃): 2.49–2.53(2H, m), 2.65–2.69(2H, m), 2.75–2.79(2H, m), 3.27–3.34(2H, m), 3.48–3.54(2H, m), 3.56–3.64(2H, m), 3.79–3.83(1H, m), 3.85(3H, s), 3.86(3H, s), 4.39–4.65 (2H, m), 6.53–6.63(2H, m). |
| 3-3 | (6,7-dimethoxy-THIQ)carbonyl-pyrrolidine with N-(2-aminoethyl) | ¹H-NMR(CDCl₃): 2.04–2.18(2H, m), 2.43–2.69(4H, m), 2.75–2.84(5H, m), 2.94–3.02(1H, m), 3.23–3.38(1H, m), 3.69–3.73(1H, m), 3.81–3.85(1H, m), 3.85(3H, s), 3.86(3H, s), 4.58–4.66 (2H, m), 6.57–6.63(2H, m). |
| 3-4 | (4,4-dimethyl-6,7-dimethoxy-THIQ)carbonyl-piperidine with N-(2-aminoethyl) | ¹H-NMR(CDCl₃): 1.24(3H, s), 1.29(3H, s), 1.58–1.84(4H, m), 1.99(1H, brs), 2.20–2.30(1H, m), 2.41–2.47(2H, m), 2.77–2.83(2H, m), 2.90–2.92(2H, m), 3.47–3.64(2H, m), 3.84–3.88(6H, m), 4.65–4.67(2H, m), 6.54–6.58(1H, m), 6.77–6.80(1H, m). |
| 4 | 4,4-dimethyl-6,7-dimethoxy-1,2,3,4-tetrahydroisoquinoline | ¹H-NMR(CDCl₃): 1.26(6H, s), 2.84(2H, s), 3.83(3H, s), 3.87(3H, s), 3.94(2H, s), 6.47(1H, s), 6.80(1H, s). |

TABLE 2

| Ex. | Structure | Salt | Data |
|---|---|---|---|
| 1 | (6,7-dimethoxy-THIQ)carbonyl-piperidine-N-propanamide-N-(3,4-dimethoxyphenyl) | HCl | m.p.: 154–156° C. ¹H-NMR(DMSO-d₆): 1.46–1.99(4H, m), 2.66–2.72(1H, m), 2.80–3.09 (6H, m), 3.36–3.64(6H, m), 3.71–3.72(12H, m), 4.45–4.70 (2H, m), 6.74–6.76(1H, m), 6.79–6.82(1H, m), 6.87–6.90(1H, m), 7.08–7.13(1H, m), 7.26–7.30(1H, m), 10.15–10.22(1H, m), 10.54(1H, brs). |
| 2 | (6,7-dimethoxy-THIQ)carbonyl-piperidine-N-propanamide-N-(benzo[1,3]dioxol-5-yl) | HCl | m.p.: 226–228° C. ¹H-NMR(DMSO-d₆): 1.49–1.97(4H, m), 2.66–2.72(1H, m), 2.80–3.12 (6H, m), 3.36–3.54(6H, m), 3.71–3.73(6H, m), 4.50–4.66 (2H, m), 6.75–6.76(1H, m), 6.79–6.82(1H, m), 6.84–6.87(1H, m), 6.96–7.00(1H, m), 7.30–7.32(1H, m), 10.25–10.34(1H, m), 10.64(1H, brs). |
| 3 | (6,7-dimethoxy-THIQ)carbonyl-piperidine-N-propanamide-N-(3,5-dimethoxyphenyl) | ½ (CO₂H)₂ | m.p.: 187–192° C. ¹H-NMR(DMSO-d₆): 1.36–1.86(4H, m), 2.33–3.76(25H, m), 4.46–4.66 (2H, m), 6.21(1H, s), 6.73(1H, m), 6.79(1H, s), 6.82(1H, s), 6.83(1H, s), 10.07(1H, s). |

TABLE 2-continued

| Ex. | Structure | Salt | Data |
|---|---|---|---|
| 4 | 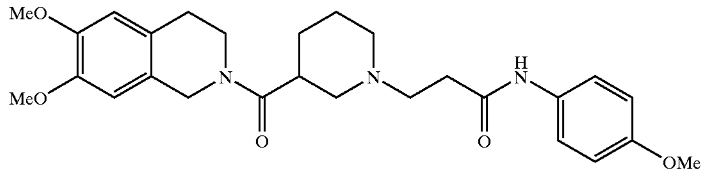 | HCl | m.p.: 211–213° C.<br>$^1$H-NMR(DMSO-$d_6$): 1.46–2.04(4H, m), 2.66–3.18(6H, m), 3.30–3.89 (16H, m), 4.45–4.70(2H, m), 6.74–6.90(4H, m), 7.49–7.52(2H, m), 10.17–10.26(1H, m), 10.70(1H, brs). |
| 5 | 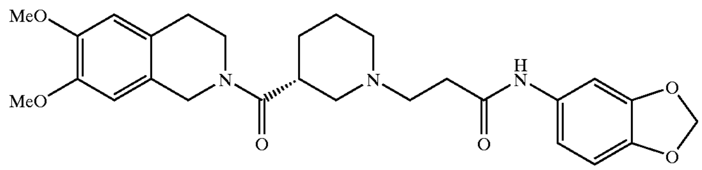 | L-TA | m.p.: 174–175° C.<br>$^1$H-NMR(DMSO-$d_6$): 1.41(1H, brs), 1.69–1.75(3H, m), 2.31(1H, brs), 2.43(1H, brs), 2.55(2H, brs), 2.66(1H, brs), 2.76(1H, brs), 2.86 (2H, brs), 3.01(3H, brs), 3.63–3.68 (2H, m), 3.71(6H, s), 4.17(2H, s), 4.45–4.61(2H, m), 5.97(2H, s), 6.73(1H, s), 6.78–6.79(1H, m), 6.83–6.85(1H, m), 6.93(1H, dd), 7.29(1H, d), 9.98(1H, s). |
| 6 | 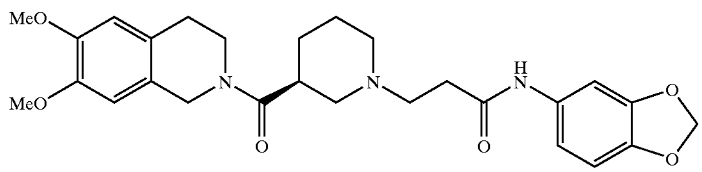 | D-TA | m.p.: 175–177° C.<br>$^1$H-NMR(DMSO-$d_6$): 1.40(1H, brs), 1.64–1.78(3H, m), 2.30(1H, brs), 2.41(1H, brs), 2.55(2H, brs), 2.66–2.67(1H, m), 2.86(2H, brs), 3.01(3H, brs), 3.60–3.65(2H, m), 3.71(6H, s), 4.17(2H, s), 4.46–4.66 (2H, m), 5.97(2H, s), 6.73(1H, s), 6.78–6.79(1H, m), 6.83–6.85(1H, m), 6.93(1H, dd), 7.29(1H, d), 9.99(1H, s). |
| 7 | 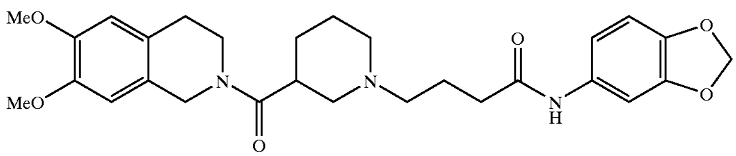 | (CO$_2$H)$_2$ | m.p.: 113–116° C. |
| 8 | 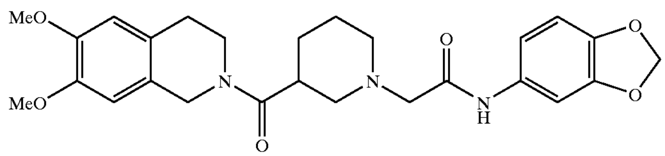 | (CO$_2$H)$_2$ | m.p.: 157–159° C. |
| 9 | 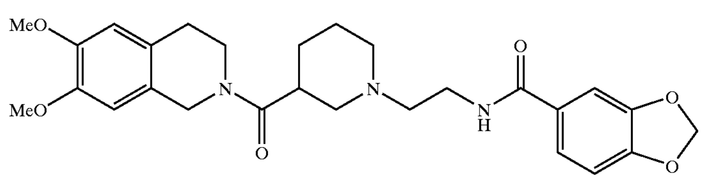 | HCl | m.p.: 182–185° C.<br>$^1$H-NMR(DMSO-$d_6$): 1.46–2.00(4H, m), 2.65–2.80(2H, m), 2.82–3.10(2H, m), 3.25(2H, brs), 3.30–3.40(1H, m), 3.50–3.80(6H, m), 3.79(3H, s), 3.80(3H, s), 4.40–4.69 (2H, m), 6.10(2H, s), 6.75–6.82(2H, m), 7.00–7.03(1H, m), 7.43–7.52(2H, m), 8.60–8.75(1H, m), 10.20(1H, brs). |
| 10 | 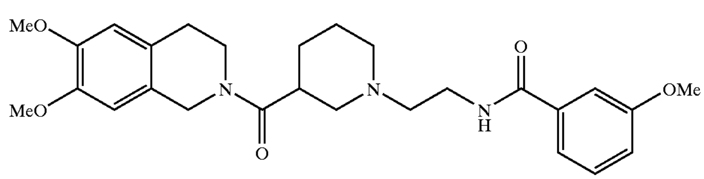 | (CO$_2$H)$_2$ | m.p.: 120–123° C.<br>H-NMR(DMSO-$d_6$): 1.52(1H, brs), 1.99(3H, brs), 2.66–2.79(2H, m), 3.10–3.45(6H, m), 3.62(2H, brs), 3.65–3.83(9H, m), 3.86(3H, s), 4.40–4.67(2H, m), 6.75(1H, s), 6.79(1H, d), 7.11(1H, d), 7.37–7.45(2H, m), 8.68(1H, brs). |

TABLE 2-continued

| Ex. | Structure | Salt | Data |
| --- | --- | --- | --- |
| 11 | 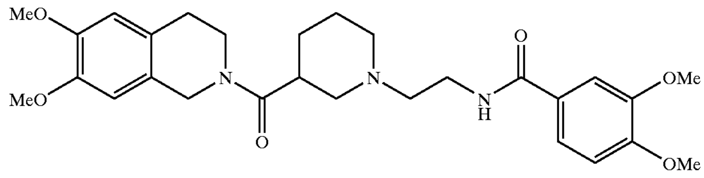 | HCl | m.p.: 199–202° C.<br>$^1$H-NMR(DMSO-d$_6$): 1.46–2.00(4H, m), 2.65–2.80(2H, m), 2.85–3.12 (2H, m), 3.26(2H, brs), 3.50–3.75 (13H, m), 3.81(3H, s), 3.82(3H, s), 4.42–4.69(2H, m), 6.75–6.83(2H, m), 7.02–7.05(1H, m), 7.50–7.55 (2H, m), 8.73–8.83(1H, m), 10.51(1H, brs). |
| 12 | 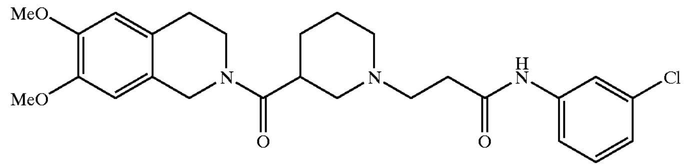 | HCl | m.p.: 181–185° C. |
| 13 | 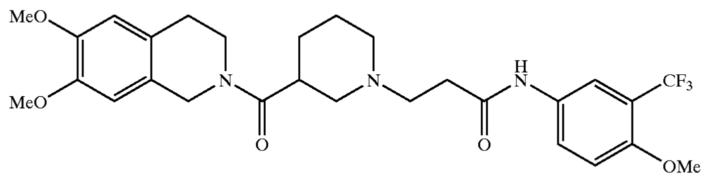 | HCl | m.p.: 166–168° C. |
| 14 | 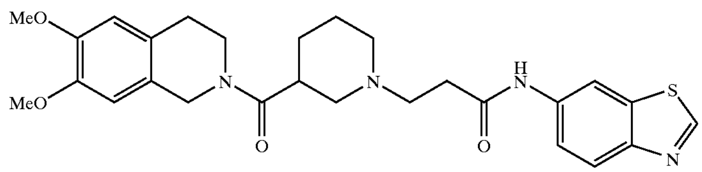 | HCl | m.p.: 183–185° C. |
| 15 | 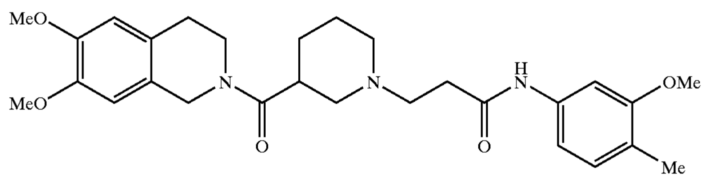 | HCl | m.p.: 171–173° C. |
| 16 | 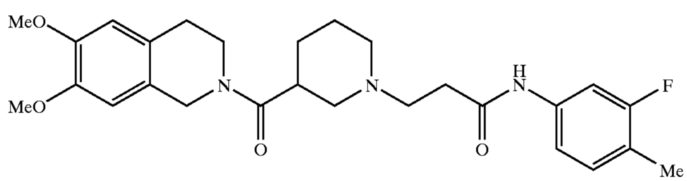 | HCl | m.p.: 183–185° C. |
| 17 | 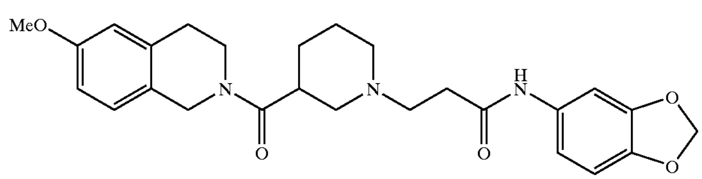 | ½ (CO$_2$H)$_2$ | m.p.: 179–180° C. |
| 18 | 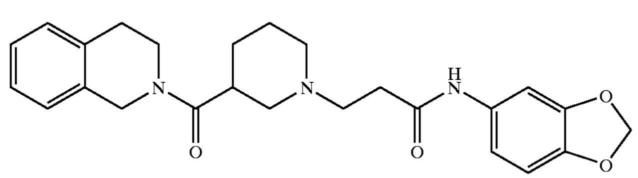 | ½ (CO$_2$H)$_2$ | m.p.: 195–196° C. |

TABLE 2-continued

| Ex. | Structure | Salt | Data |
|---|---|---|---|
| 19 | 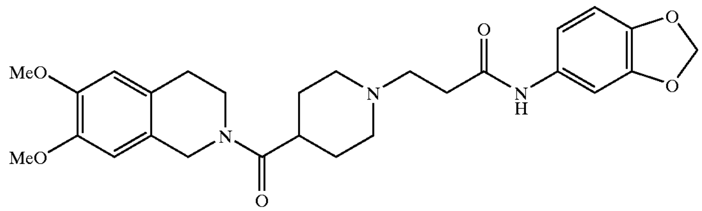 | HCl | m.p.: 203–206° C. |
| 20 | 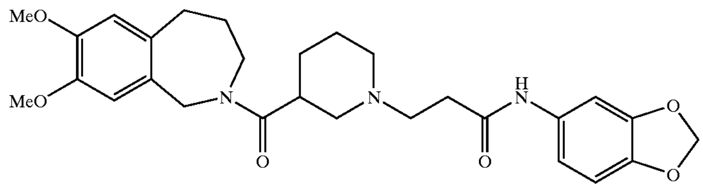 | ½ (CO$_2$H)$_2$ | m.p.: 180–181° C. |
| 21 | 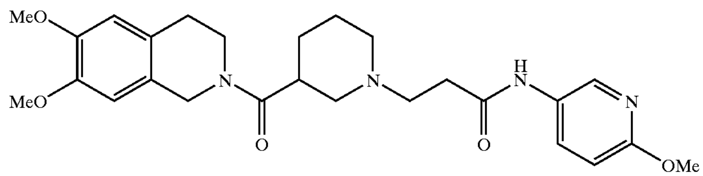 | (CO$_2$H)$_2$ | m.p.: 182–185° C. |
| 22 | 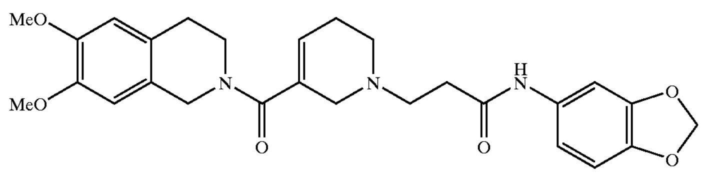 | — | m.p.: 159–160° C. |
| 23 | 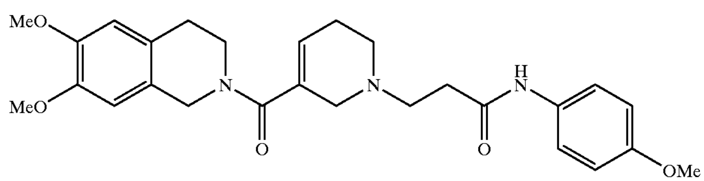 | — | m.p.: 155–164° C. |
| 24 | 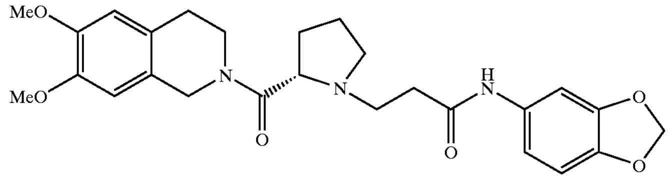 | (CO$_2$H)$_2$ | $^1$H-NMR(DMSO-d$_6$): 1.83(3H, brs), 1.99(1H, brs), 2.68–2.81(5H, m), 3.54–3.68(6H, m), 3.71–3.73(6H, m), 4.48–4.66(2H, m), 5.95–5.96(2H, m), 6.73–6.82 (3H, m), 6.97(1H, brs), 7.28(1H, s), 10.29(1H, brs). |
| 25 | 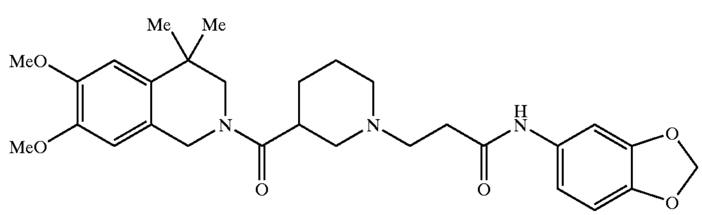 | HCl | m.p.: 225–228° C. |
| 26 | 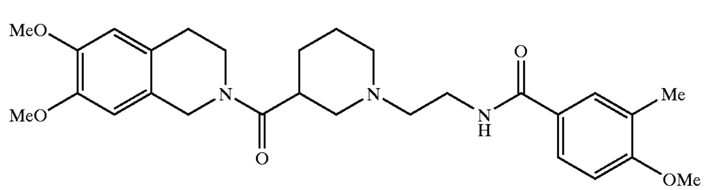 | (CO$_2$H)$_2$ | m.p.: 114–117° C. |

TABLE 2-continued

| Ex. | Structure | Salt | Data |
|---|---|---|---|
| 27 | MeO-[tetrahydroisoquinoline(6,7-diOMe)]-C(O)-[piperidine-3-yl]-N-CH2CH2-NH-C(O)-[phenyl-3-F-4-OMe] | $(CO_2H)_2$ | m.p.: 113–116° C. |
| 28 | MeO-[tetrahydroisoquinoline(6,7-diOMe)]-C(O)-[piperidine-3-yl]-N-CH2CH2-NH-C(O)-[phenyl-3-OMe-4-Me] | $(CO_2H)_2$ | m.p.: 125–128° C. |
| 29 | MeO-[tetrahydroisoquinoline(6,7-diOMe)]-C(O)-[piperidine-3-yl]-N-CH2CH2-NH-C(O)-[phenyl-3,4-diF] | $(CO_2H)_2$ | m.p.: 120–124° C. |
| 30 | MeO-[tetrahydroisoquinoline(6,7-diOMe)]-C(O)-[piperidine-3-yl]-N-CH2CH2-NH-C(O)-[benzo-1,4-dioxin-6-yl] | $(CO_2H)_2$ | m.p.: 126–130° C. |
| 31 | MeO-[tetrahydroisoquinoline(6,7-diOMe)]-C(O)-[piperidine-3-yl]-N-CH2CH2-NH-C(O)-[2,2-difluoro-benzo-1,3-dioxol-5-yl] | $(CO_2H)_2$ | m.p.: 113–116° C. |
| 32 | MeO-[tetrahydroisoquinoline(6,7-diOMe)]-C(O)-[piperidine-3-yl]-N-CH2CH2-NH-C(O)-[phenyl-4-OEt] | $(CO_2H)_2$ | m.p.: 125–127° C. |
| 33 | MeO-[tetrahydroisoquinoline(6,7-diOMe)]-C(O)-[piperidine-3-yl]-N-CH2CH2-NH-C(O)-[phenyl-4-OiPr] | $(CO_2H)_2$ | m.p.: 116–119° C. |
| 34 | MeO-[tetrahydroisoquinoline(6,7-diOMe)]-C(O)-[piperidine-3-yl]-N-CH2CH2-NH-C(O)-[4-methyl-3-oxo-3,4-dihydro-2H-benzo[1,4]oxazin-7-yl] | $(CO_2H)_2$ | m.p.: 130–138° C. |

TABLE 2-continued

| Ex. | Structure | Salt | Data |
|---|---|---|---|
| 35 | (structure) | (CO₂H)₂ | m.p.: 124–133° C. |
| 36 | (structure) | (CO₂H)₂ | H-NMR(DMSO-d₆): 1.53(1H, brs), 1.82(3H, brs), 2.67–2.69(1H, m), 2.78–3.36(9H, m), 3.59–3.68(3H, m), 3.71(6H, s), 4.46–4.68(2H, m), 6.74–6.81(2H, m), 8.12–8.19(2H, m), 8.60–8.61(1H, m), 9.08(1H, s). |
| 37 | (structure) | — | m.p.: 150–151° C.<br>[α]D = −37.0° (CHCl₃, C = 1.0) |
| 38 | (structure) | — | m.p.: 154–155° C.<br>[α]D = +35.8° (CHCl₃, C = 1.0) |
| 39 | (structure) | (CO₂H)₂ | H-NMR(DMSO-d₆): 1.52(1H, brs), 1.81(3H, brs), 2.68–2.69(1H, m), 2.78–3.35(9H, m), 3.60–3.70(3H, m), 3.71(3H, s), 3.71(3H, s), 4.46–4.68(2H, m), 6.53(1H, s), 6.74–6.82(2H, m), 7.42–7.44(2H, m), 7.63–7.65(1H, m), 8.14(1H, s), 8.53(1H, s), 11.36(1H, s). |
| 40 | (structure) | (CO₂H)₂ | m.p.: 137–141° C. |
| 41 | (structure) | (CO₂H)₂ | m.p.: 133–136° C. |
| 42 | (structure) | (CO₂H)₂ | m.p.: 166–167° C. |

TABLE 2-continued

| Ex. | Structure | Salt | Data |
|---|---|---|---|
| 43 | [MeO, MeO-tetrahydroisoquinoline-C(O)-piperidine-CH2CH2-NH-C(O)-2,4-difluorophenyl] | (CO$_2$H)$_2$ | m.p.: 178–180° C. |
| 44 | [MeO, MeO-tetrahydroisoquinoline-C(O)-piperidine-CH2CH2-NH-C(O)-3-CF3-4-F-phenyl] | H$_3$PO$_4$ | m.p.: 186–188° C. |
| 45 | [MeO, MeO-tetrahydroisoquinoline-C(O)-piperidine-CH2CH2-NH-C(O)-3-Cl-4-F-phenyl] | (CO$_2$H)$_2$ | m.p.: 111–112° C. |
| 46 | [MeO, MeO-tetrahydroisoquinoline-C(O)-tetrahydropyridine-CH2CH2-NH-C(O)-benzodioxole] | — | m.p.: 162–164° C. |
| 47 | [MeO, MeO-tetrahydroisoquinoline-C(O)-tetrahydropyridine-CH2CH2-NH-C(O)-4-OMe-phenyl] | — | m.p.: 153–154° C. |
| 48 | [MeO, MeO-tetrahydroisoquinoline-C(O)-azetidine-CH2CH2-NH-C(O)-benzodioxole] | — | m.p.: 131–133° C. |
| 49 | [MeO, MeO-tetrahydroisoquinoline-C(O)-(S)-piperidine-CH2CH2-NH-C(O)-4-F-phenyl] | H$_3$PO$_4$ | m.p.: 197–199° C. [α]D = −20.0° (H$_2$O, C = 1.0) |
| 50 | [MeO, MeO-tetrahydroisoquinoline-C(O)-(R)-piperidine-CH2CH2-NH-C(O)-4-F-phenyl] | H$_3$PO$_4$ | m.p.: 187–191° C. [α]D = +20.5° (H$_2$O, C = 1.0) |

TABLE 2-continued
| Ex. | Structure | Salt | Data |
|---|---|---|---|
| 51 | 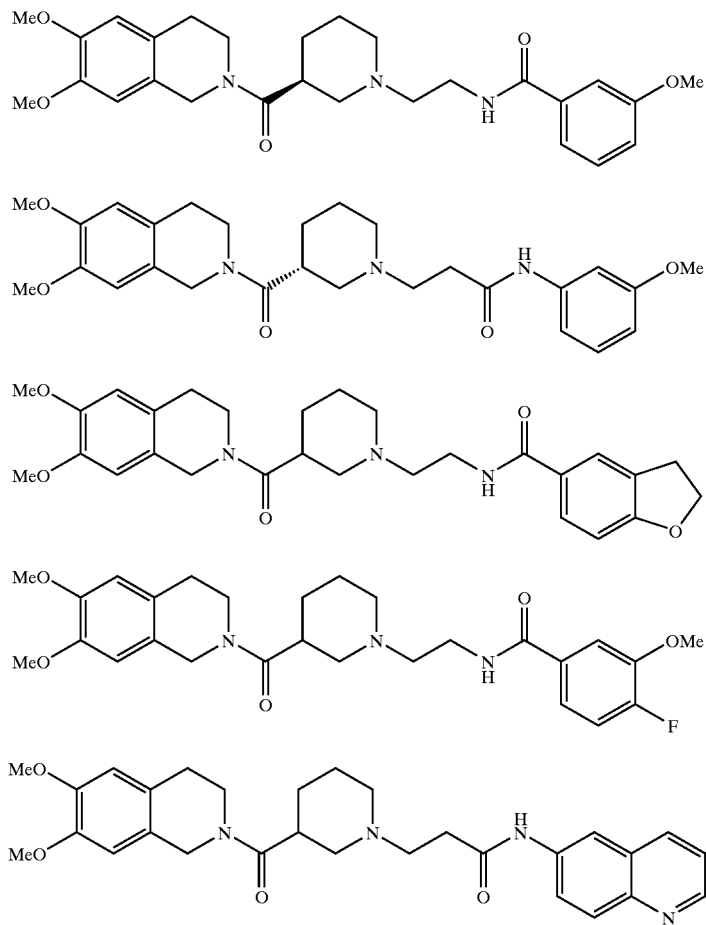 | (CO$_2$H)$_2$ | m.p.: 138–140° C. |
| 52 | 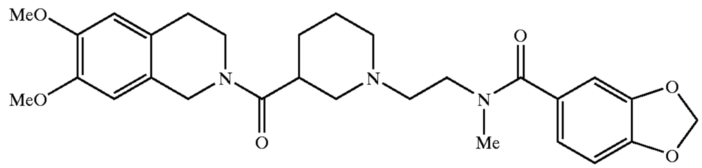 | (CO$_2$H)$_2$ | 1-NMR(DMSO-d$_6$): 1.49(1H, brs), 1.76(3H, brs), 2.62–3.12(10H, m), 2.94–2.95(3H, m), 3.70(3H, brs), 3.70(3H, s), 3.71(3H, s), 4.47–4.61 (2H, m), 6.06(2H, s), 6.74(1H, s), 6.79(1H, d), 6.95–7.02(3H, m). |
| 53 | 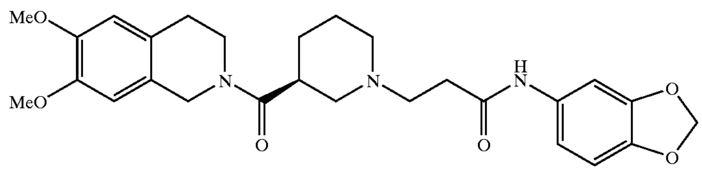 | Fu | m.p.: 164–166° C. [α]D = +8.0° (H$_2$O, C = 1.0) |
TABLE 3

TABLE 3-continued
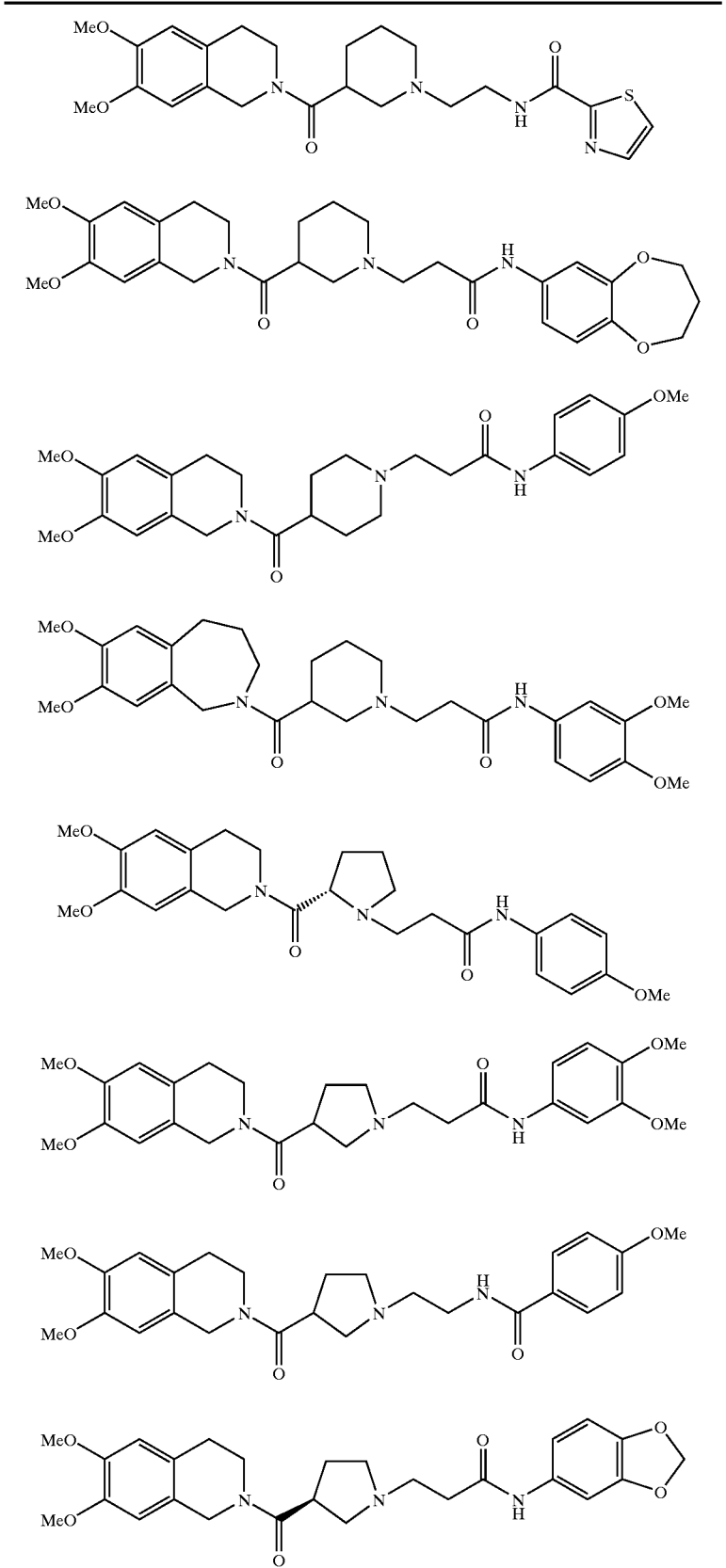

TABLE 3-continued
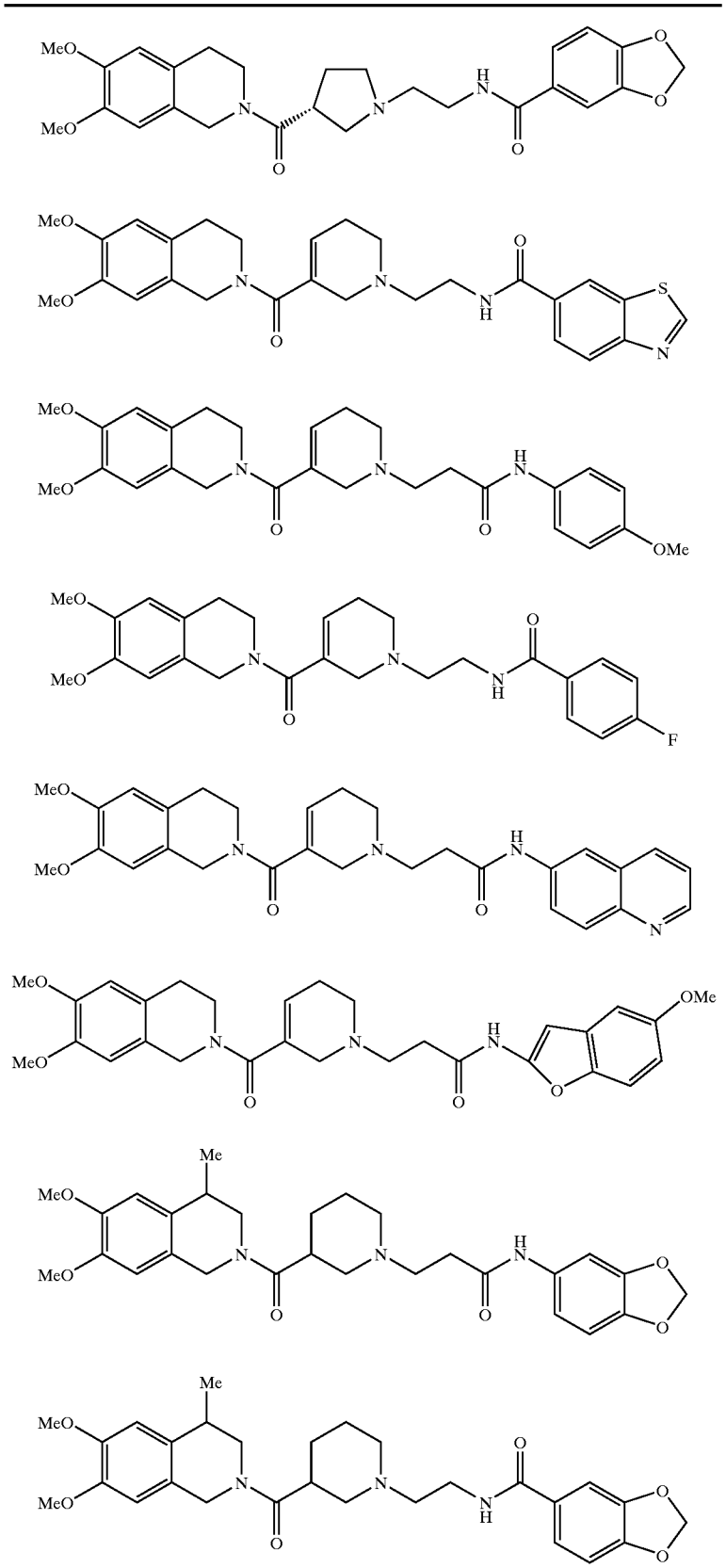

TABLE 3-continued
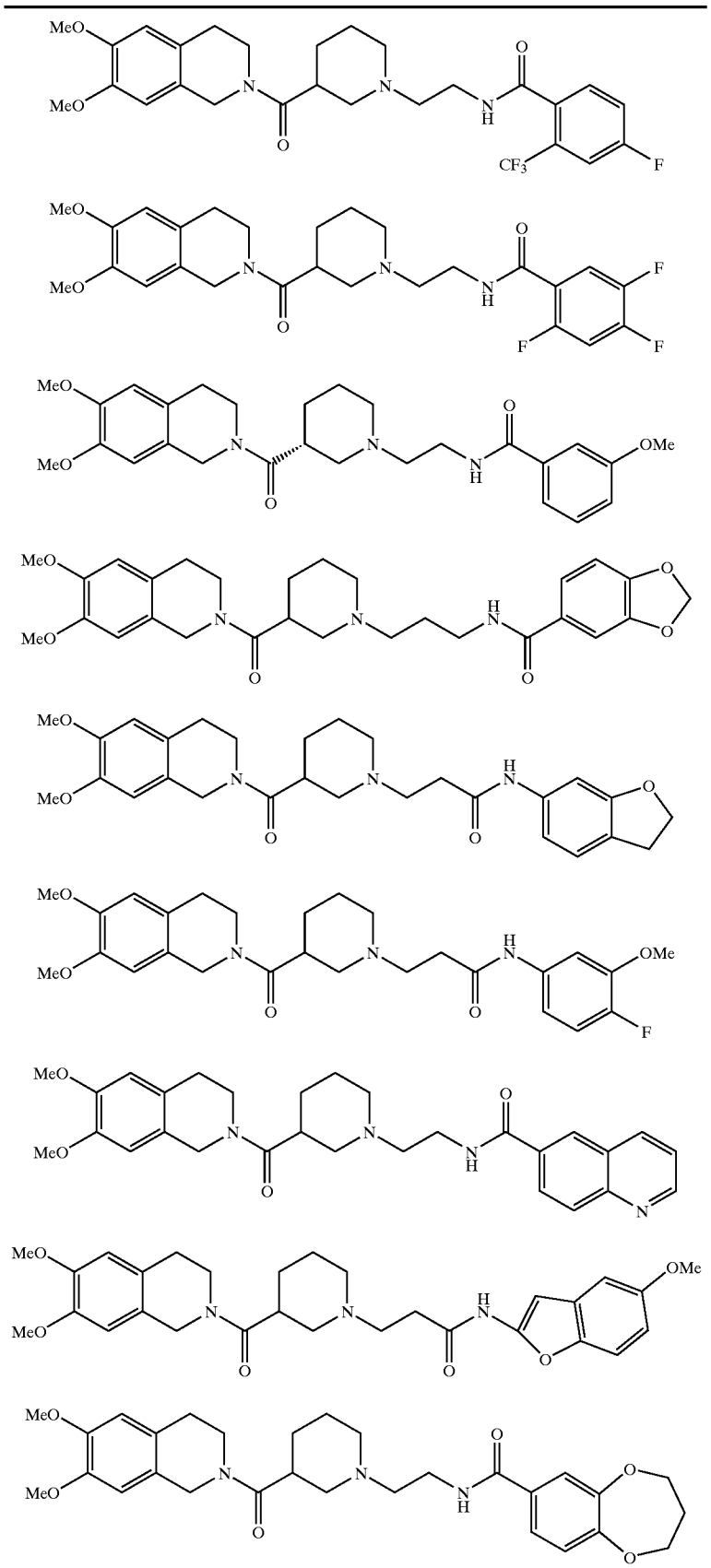

TABLE 3-continued
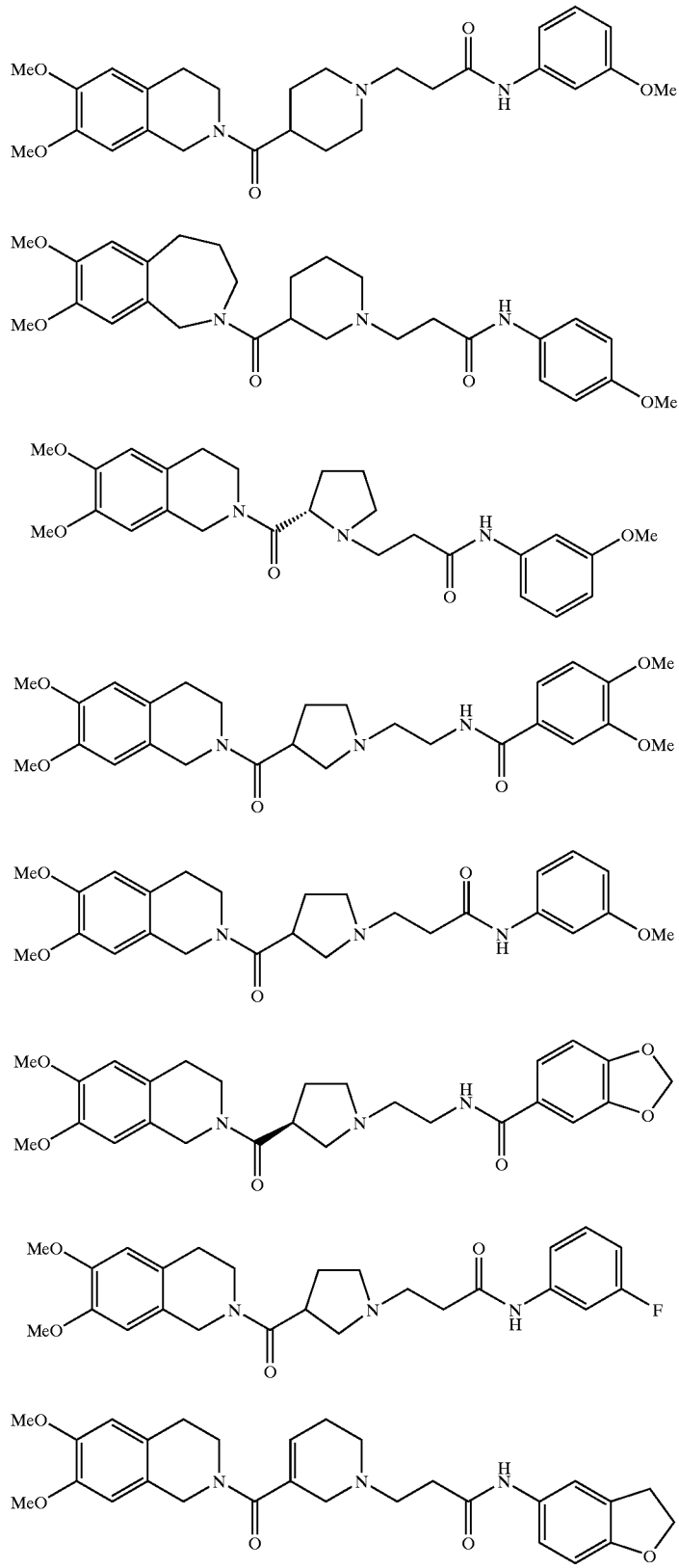

TABLE 3-continued
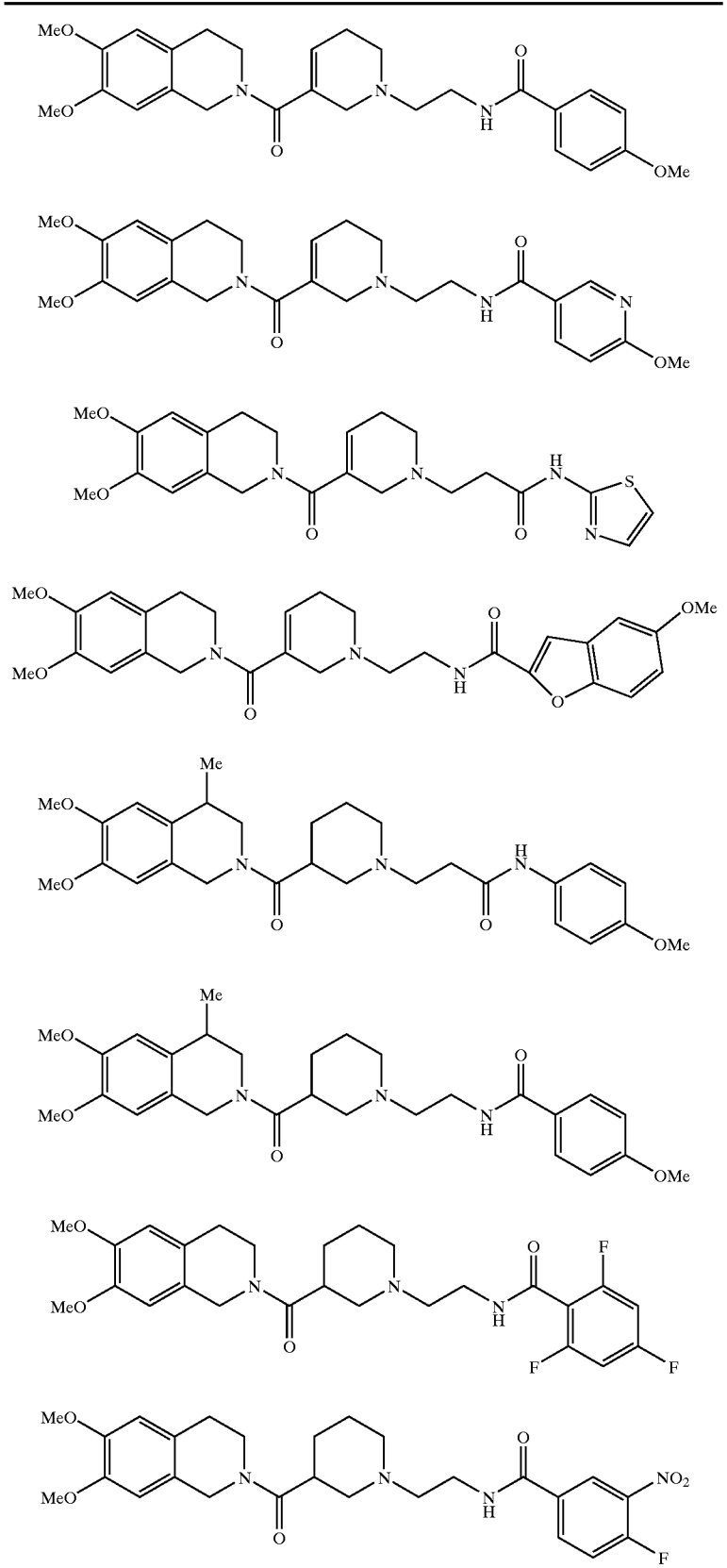

TABLE 3-continued
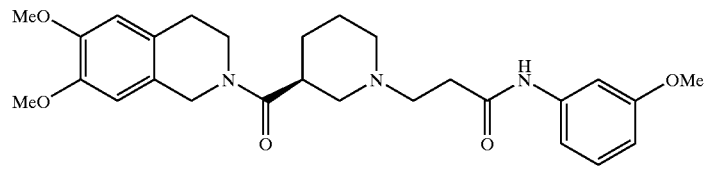
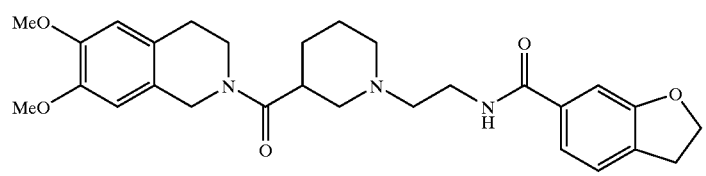
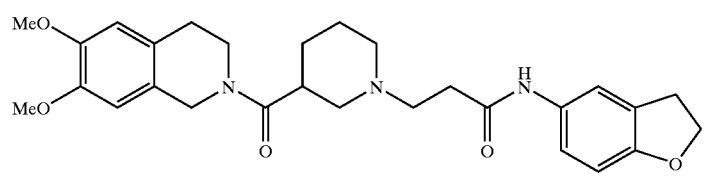
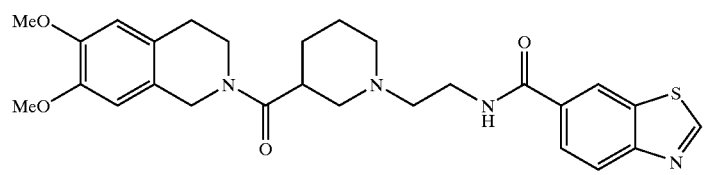
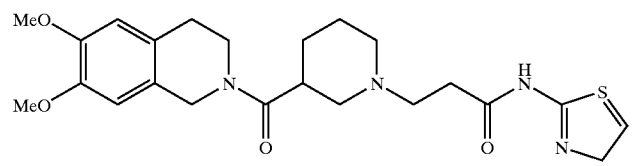
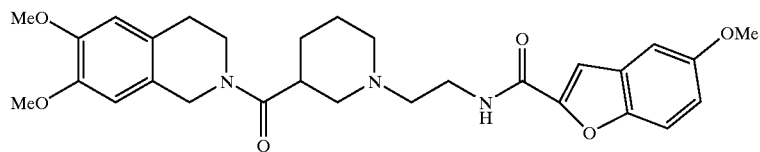
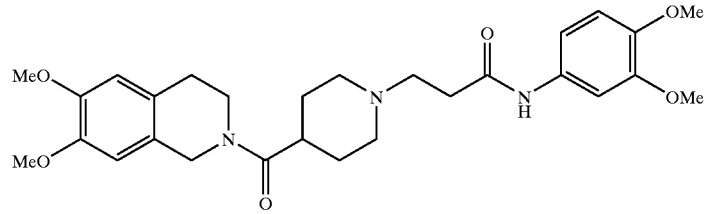
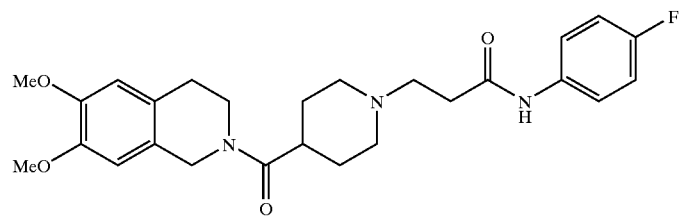

TABLE 3-continued
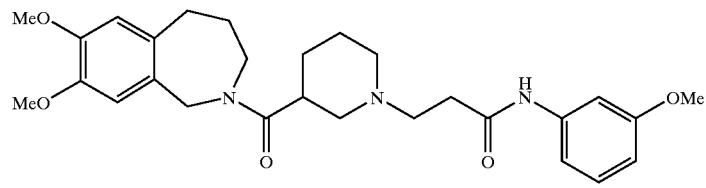
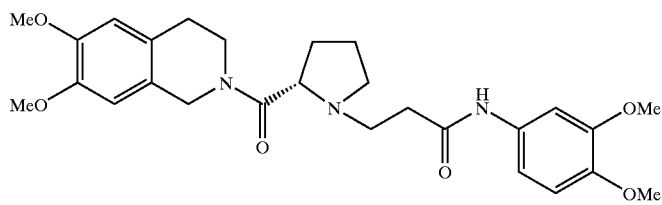
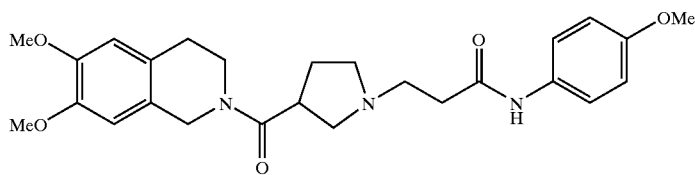
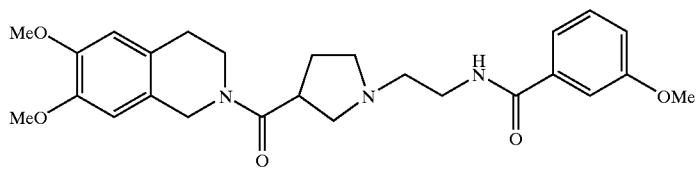
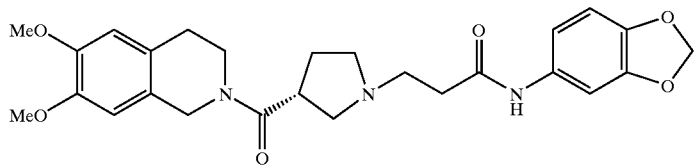
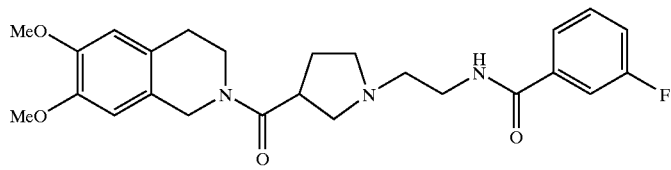
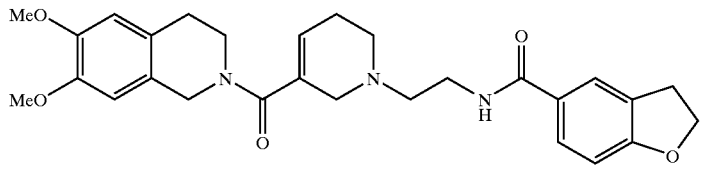
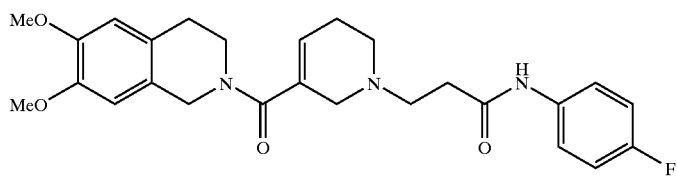

TABLE 3-continued
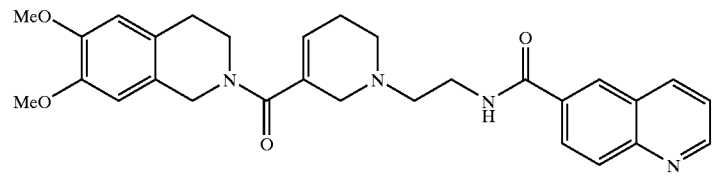
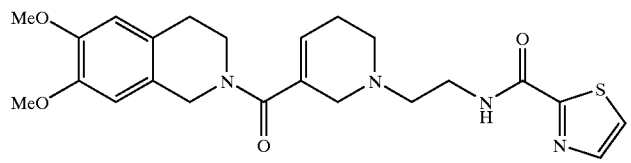
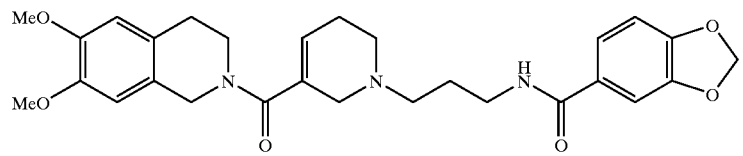
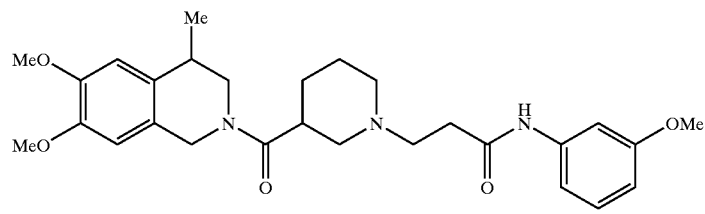
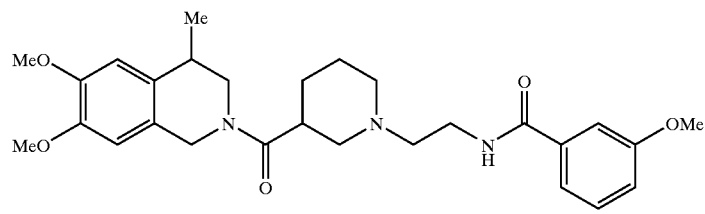
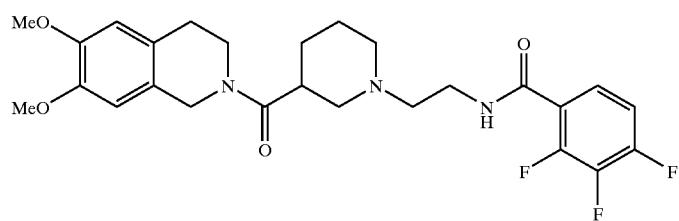
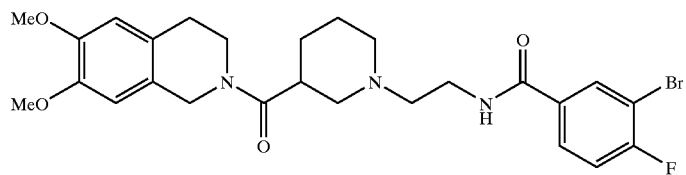

What is claimed is:

1. An isoquinoline derivative represented by the following general formula (I) or a salt thereof:

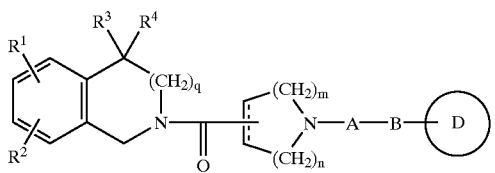

(in the formula, the symbols have the following meanings:
A: lower alkylene;
B: —C(=O)—NR⁵— or —NR⁵—C(=O)—;
R¹ and R²: hydrogen atom, lower alkyl or —O-lower alkyl, which may be the same or different;
R³, R⁴ and R⁵: hydrogen atom or lower alkyl, which may be the same or different;
ring D: optionally substituted hydrocarbon ring or optionally substituted hetero ring;
m: 1, 2 or 3;
n: 0 or 1; and
q: 1 or 2.)

2. An isoquinoline derivative represented by the following general formula (I') or a salt thereof:

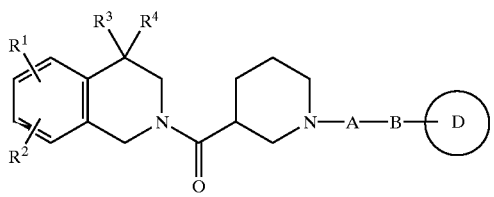

(in the formula, the symbols have the following meanings:
A: lower alkylene;
B: —C(=O)—NR⁵— or —NR⁵—C(=O)—;
R¹ and R²: hydrogen atom, lower alkyl or —O-lower alkyl, which may be the same or different;
R³, R⁴ and R⁵: hydrogen atom or lower alkyl, which may be the same or different; and
ring D: optionally substituted hydrocarbon ring or optionally substituted hetero ring.)

3. N-{2-[3-(6,7-Dimethoxy-1,2,3,4-tetrahydroisoquinoline-2-carbonyl)piperidino]ethyl}-4-fluorobenzamide; N-{2-[3-(6,7-dimethoxy-1,2,3,4-tetrahydroisoquinoline-2-carbonyl)piperidino]ethyl}-3,4-methylenedioxybenzamide; 3-[3-(6,7-dimethoxy-1,2,3,4-tetrahydroisoquinoline-2-carbonyl)piperidino]-N-(3,4-methylenedioxyphenyl)propanamide; N-{2-[3-(6,7-dimethoxy-1,2,3,4-tetrahydroisoquinoline-2-carbonyl)piperidino]ethyl}-4-methoxy-3-methylbenzamide; N-{2-[3-(6,7-dimethoxy-1,2,3,4-tetrahydroisoquinoline-2-carbonyl)piperidino]ethyl}-3-methoxybenzamide; N-{2-[3-(6,7-dimethoxy-1,2,3,4-tetrahydroisoquinoline-2-carbonyl)piperidino]ethyl}-3,4-difluorobenzamide, or salts thereof.

4. A pharmaceutical composition containing the isoquinoline derivative or salt thereof according to claim 1 as an effective ingredient.

5. The pharmaceutical composition according to claim 4, having a $I_f$ current inhibitory effect.

6. The pharmaceutical composition according to claim 4, having a cardiac rate lowering effect.

* * * * *

UNITED STATES PATENT AND TRADEMARK OFFICE
CERTIFICATE OF CORRECTION

PATENT NO. : 6,573,279 B1
DATED : June 3, 2003
INVENTOR(S) : Watanabe et al.

It is certified that error appears in the above-identified patent and that said Letters Patent is hereby corrected as shown below:

Title page,
After Item [76], insert -- [73]   Assignee: Yamanouchi Pharmaceutical Co., Ltd., Tokyo (JP) --.
After the *Assistant Examiner*, insert -- *Attorney, Agent, or Firm*-Finnegan, Henderson, Farabow, Garrett & Dunner, L.L.P. --.

Signed and Sealed this

Twenty-eighth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,573,279 B1
DATED : June 3, 2003
INVENTOR(S) : Watanabe et al.

It is certified that error appears in the above-identified patent and that said Letters Patent is hereby corrected as shown below:

Column 19,
Table 1, compound 2-3:

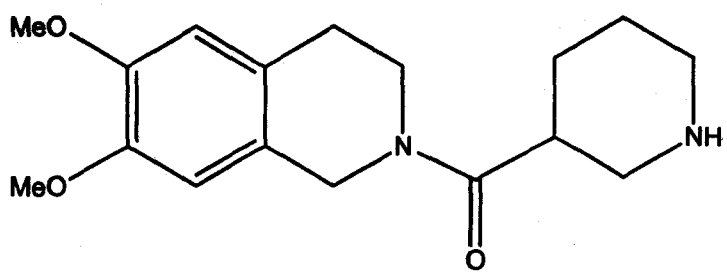

should read

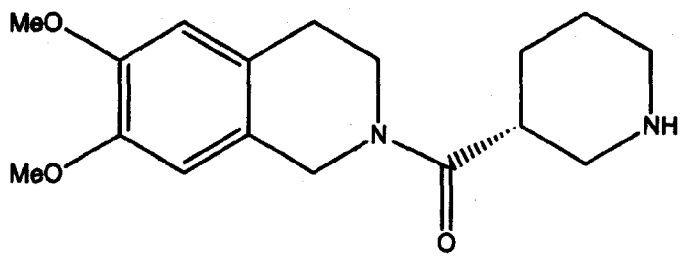

Column 21,
Table 1, compound 2-4:

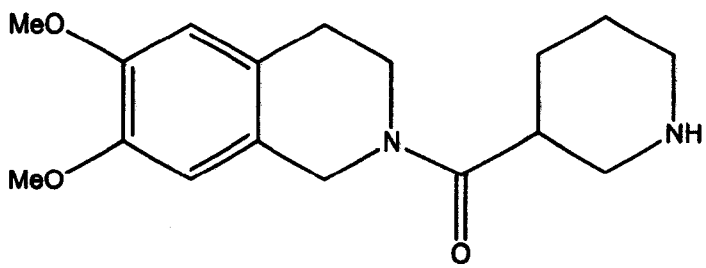

should read

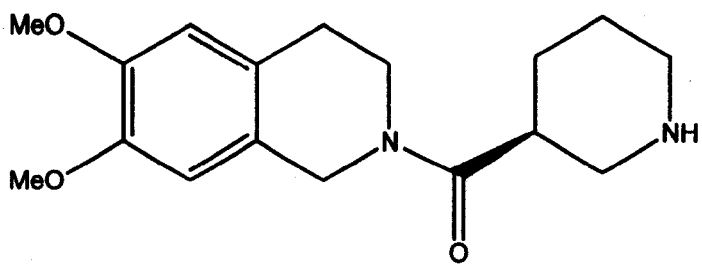

UNITED STATES PATENT AND TRADEMARK OFFICE
CERTIFICATE OF CORRECTION

PATENT NO. : 6,573,279 B1
DATED : June 3, 2003
INVENTOR(S) : Watanabe et al.

It is certified that error appears in the above-identified patent and that said Letters Patent is hereby corrected as shown below:

Column 21 (cont'd),
Table 1, compound 2-7:

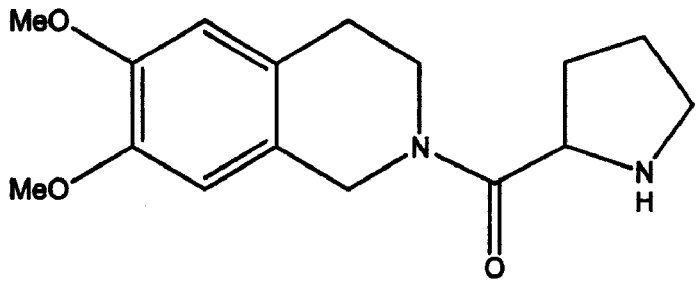

should read

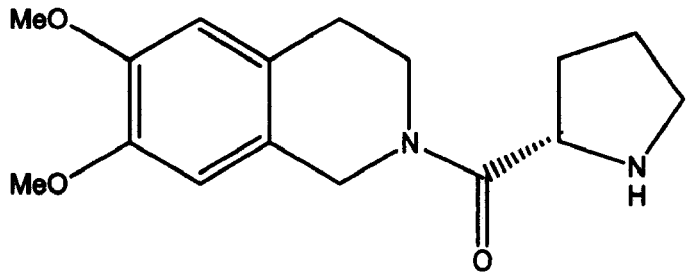

Signed and Sealed this

Seventeenth Day of February, 2004

JON W. DUDAS
*Acting Director of the United States Patent and Trademark Office*